US010521805B2

(12) United States Patent
Yurach et al.

(10) Patent No.: US 10,521,805 B2
(45) Date of Patent: Dec. 31, 2019

(54) TECHNIQUES FOR QUALIFICATION AND MAINTENANCE OF SCIENTIFIC INFORMATION SYSTEM DEVICES

(75) Inventors: Dana Yurach, Mendon, MA (US); Peter Bastek, Bellingham, MA (US); Catalin Ristache, Brasov (RO)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 830 days.

(21) Appl. No.: 14/118,606

(22) PCT Filed: Jun. 13, 2012

(86) PCT No.: PCT/US2012/042194
§ 371 (c)(1),
(2), (4) Date: Feb. 4, 2014

(87) PCT Pub. No.: WO2012/174077
PCT Pub. Date: Dec. 20, 2012

(65) Prior Publication Data

US 2014/0195446 A1 Jul. 10, 2014

Related U.S. Application Data

(60) Provisional application No. 61/497,104, filed on Jun. 15, 2011.

(51) Int. Cl.
*G01D 18/00* (2006.01)
*G06Q 30/02* (2012.01)
(Continued)

(52) U.S. Cl.
CPC ....... *G06Q 30/018* (2013.01); *G06F 11/3055* (2013.01)

(58) Field of Classification Search
CPC ......... G06Q 30/00; G06Q 30/02; G01D 18/00
(Continued)

(56) References Cited

U.S. PATENT DOCUMENTS 5,366,896 A 11/1994 Margrey et al.
6,556,949 B1 4/2003 Lyon
(Continued)

OTHER PUBLICATIONS

International Search Authority (ISA/US), Search Report dated Aug. 7, 2012.
(Continued)

*Primary Examiner* — Marilyn G Macasiano

(57) ABSTRACT

Described are techniques for determining a qualification status of a device in a system. An occurrence of a trigger event for the device is determined. The trigger event is caused by an occurrence of any of a time-based event, a performance-based event, a usage-based event, and an unscheduled event. A user notification is provided to perform a first action responsive to the occurrence. The first action is an action to perform any of a maintenance activity, a repair activity, and a test for the device. The qualification status of the device is updated in accordance with said first action. Also described are techniques for more generally determining a compliance status of a device where the compliance status may be related to any one or more of qualification, verification, validation and/or calibration of the device.

27 Claims, 24 Drawing Sheets

(51) Int. Cl.
*G06Q 30/00* (2012.01)
*G06F 11/30* (2006.01)

(58) Field of Classification Search
USPC ............. 604/66, 67; 434/48, 43; 705/7, 305; 702/182, 33; 726/34; 417/437
See application file for complete search history.

(56) References Cited

U.S. PATENT DOCUMENTS

| | | | | |
|---|---|---|---|---|
| 7,519,905 | B2 | 4/2009 | Kougiouris et al. | |
| 2003/0236998 | A1* | 12/2003 | Gilstrap | G06F 21/445 726/34 |
| 2005/0065842 | A1* | 3/2005 | Summers | G06Q 10/06 705/305 |
| 2005/0197786 | A1 | 9/2005 | Kataria et al. | |
| 2009/0162227 | A1* | 6/2009 | Aso | F16K 31/508 417/437 |
| 2010/0160855 | A1 | 6/2010 | Bernini et al. | |
| 2010/0274603 | A1 | 10/2010 | Walker et al. | |

OTHER PUBLICATIONS

Applied Biosystems, "Smart Monitoring Service," Apr. 2006.
"UNIFI: A Revolutionary Scientific Information System Supporting Biotherapeutic LC/High Resolution MS Studies in both Non-Regulated and GXP Laboratories," WCBP, Washington, D.C., Jan. 10-12, 2011.
International Preliminary Report on Patentability dated Jan. 3, 2014.

* cited by examiner

COMPUTERS: LIST & CONFIG'N - CONTD

INSTALLED UPDATES

| | DATE/TIME | NAME |
|---|---|---|
| 1 | MAY 17, 2010 14:20:16 UTC (00:00) | SECURITY UPDATE FOR WINDOWS 7 FOR x64-BASED SYSTEMS (KB978601) |
| 2 | MAY 17, 2010 14:20:14 UTC (00:00) | SECURITY UPDATE FOR WINDOWS 7 FOR x64-BASED SYSTEMS (KB979309) |
| 3 | MAY 17, 2010 14:20:12 UTC (00:00) | CUMULATIVE SECURITY UPDATE FOR ACTIVEX KILLBITS FOR WINDOWS 7 FOR x64-BASED SYSTEMS (KB978262) |
| 4 | MAY 17, 2010 14:20:08 UTC (00:00) | WINDOWS MALICIOUS SOFTWARE REMOVAL TOOL x64 - MAY 2010 (KB890830) |
| 5 | JAN 26, 2010 19:35:02 UTC (00:00) | SECURITY UPDATE FOR WINDOWS 7 FOR x64-BASED SYSTEMS (KB972270) |
| 6 | JAN 26, 2010 19:34:53 UTC (00:00) | WINDOWS MALICIOUS SOFTWARE REMOVAL TOOL x64 - JANUARY 2010 (KB890830) |

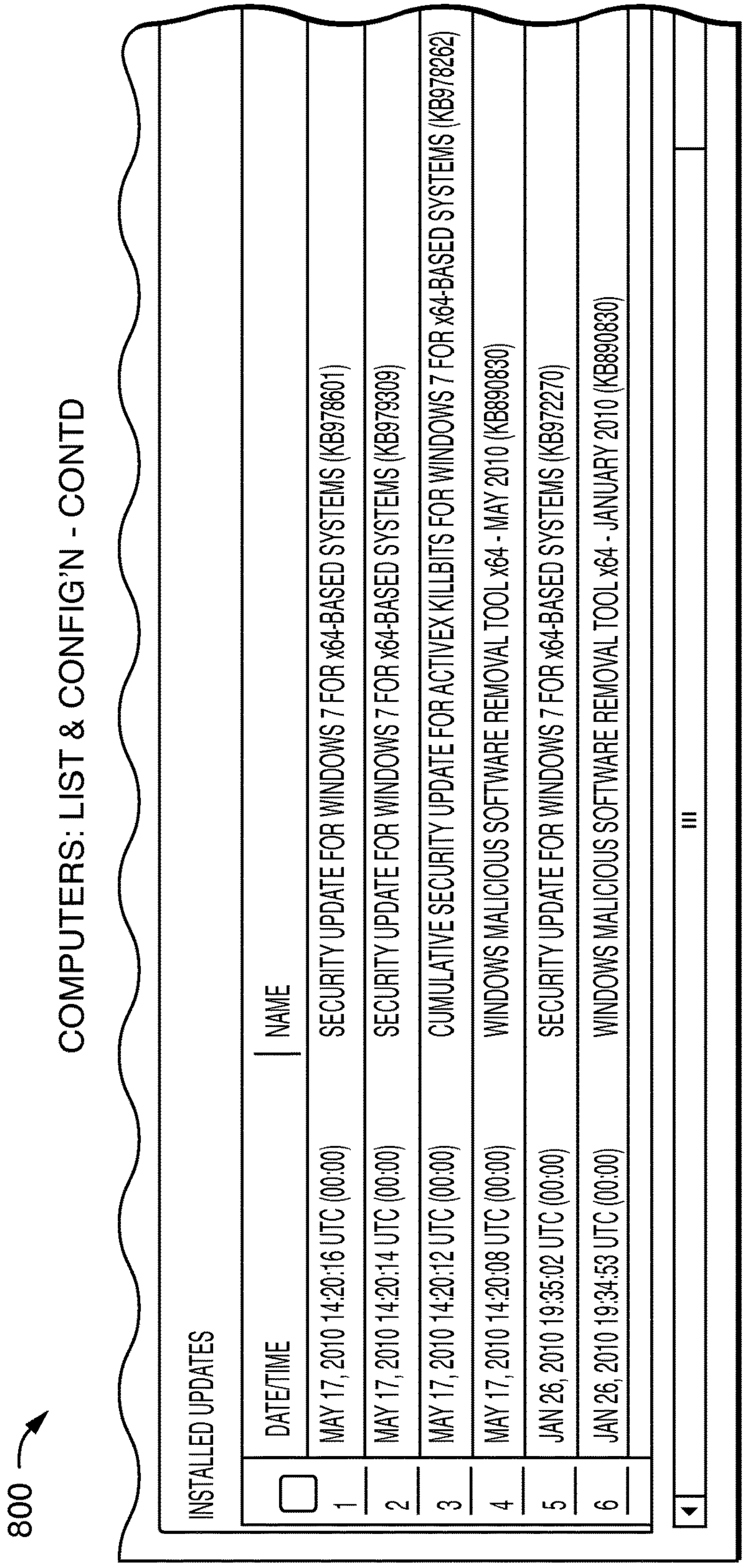

FIG. 10

MAINTENANCE LOG: INSTRUMENT

WATERS UNIFI - QUALIFICATION AND MAINTENANCE
MY WORK | WELCOME TO UNIFI | ADMINSTRATION | QUA

QUALIFICATION AND MAINTENANCE

HOME ▶ MAINTAIN ▶ MAINTAIN INSTRUMENTS ▶ MAINTENANCE LOG

INPUT SERVICE DOCUMENT OR SERVICE INFORMATION REGARDING THIS MAINTENANCE OPERATION:

MAINTENANCE DETAILS

- *MAINTENANCE ON COMPONENT: ACQUITY SAMPLE MANAGER — 1102
- *SERIAL NUMBER: ACQUITY SAMPLE MANAGER — 1104
- *MAINTENANCE OPERATION: ACQUITY PDA DETECTOR — 1106
- SERVICE COMPLETION DATE: ACQUITY BINARY SOLVENT MANAGER / MAY 17, 2010 — 1107
- PERFORMED BY: ADMINISTRATOR, UNIFI — 1108
- NEXT SERVICE DUE DATE: MAY 17, 2011 — 1110
- APPROVED BY: — 1112
- COMMENTS: — 1114

1100

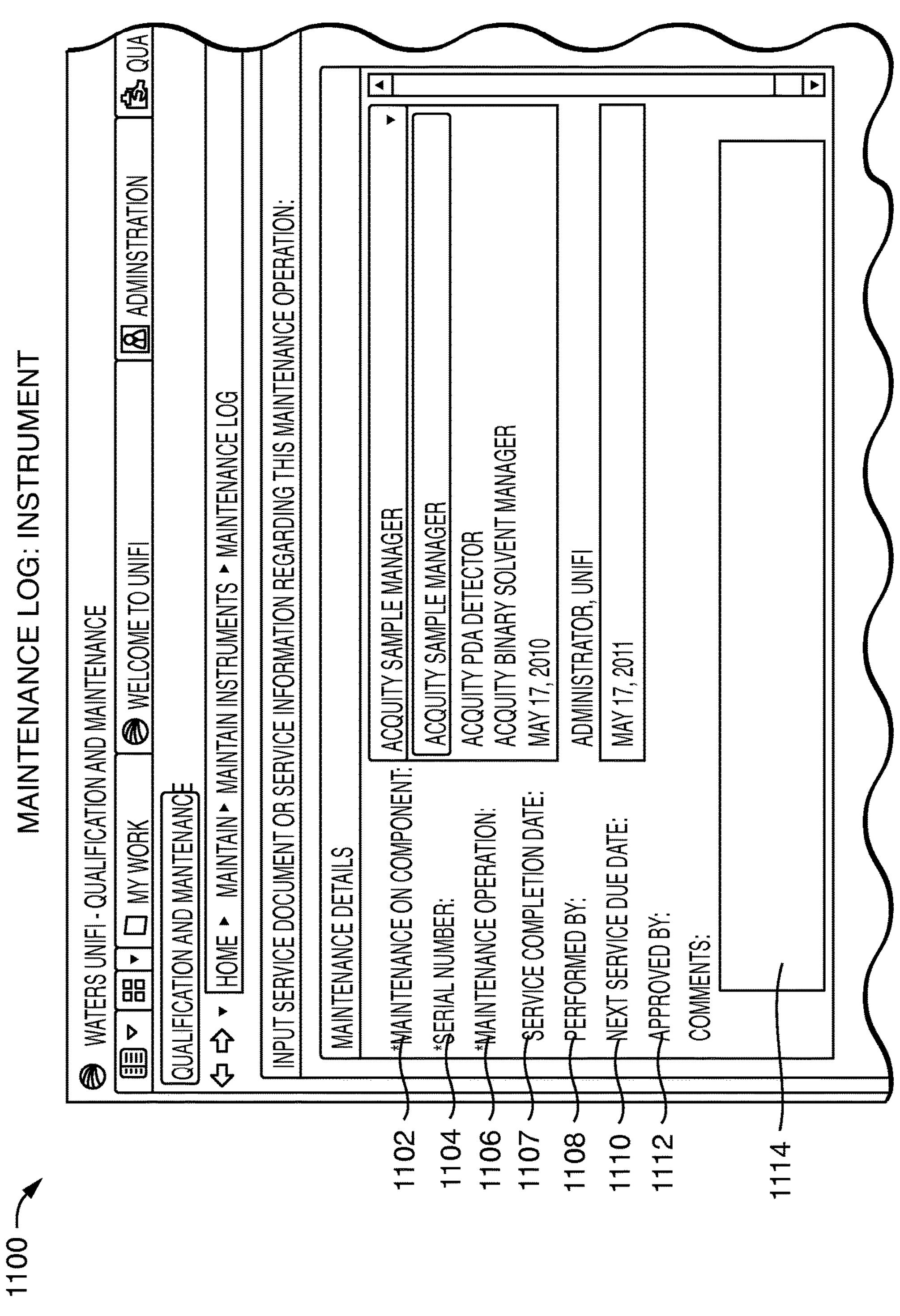

FIG. 13

MAINTENANCE LOG: INSTRUMENT

INPUT SERVICE DOCUMENT OR SERVICE INFORMATION REGARDING THIS MAINTENANCE OPERATION.

MAINTENANCE DETAILS — 1210

| | |
|---|---|
| *MAINTENANCE ON COMPONENT: | ACQUITY SAMPLE MANAGER |
| *SERIAL NUMBER: | F09UPA488M |
| *MAINTENANCE OPERATION: | PERFORMANCE MAINTENANCE |
| SERVICE COMPLETION DATE: | MAY 17, 2010 |
| PERFORMED BY: | ADMINISTRATOR, UNIFI |
| NEXT SERVICE DUE DATE: | AUG 16, 2011 |
| APPROVED BY: | |
| COMMENTS: | PERFORMANCE MAINTENANCE |

REPAIR DETAILS — 1220

| | |
|---|---|
| REPAIR REASON: | PREVENTIVE — 1222 |
| REPAIR DESCRIPTION: | SAMPLE MANAGER NEEDLE & SEALS REPLACED, SEAL PACK RECALIBRATED. — 1224 |
| REPAIR TYPE: | ROUTINE |
| *REPAIR STATUS: | COMPLETE |
| REPAIR SEVERITY: | MODERATE |

1226, 1228, 1229

TRACKING AND TRENDING — 1240

| | |
|---|---|
| REPAIR PROVIDER: | WATERS |
| LABOR EXPENSE: | 0 |
| PARTS EXPENSE: | 0 |
| FIRST TIME REPAIR: | ☑ |
| FALLOW ON REPAIR: | ☐ |
| COST CENTER: | US01 |
| TOTAL DOWNTIME (HOURS): | 4 |
| TIME TO REPAIR (HOURS): | 3 |

SUPPORTING DOCUMENTATION — 1230

ADD   OPEN   REMOVE

| | FILE NAME | DESCRIPTION | ORIGIN | CATEGORY |
|---|---|---|---|---|
| ☐ 1 | TRAINING CERTIFICATE.PDF | | FILE SYSTEM | ATTACHMENT |

1200

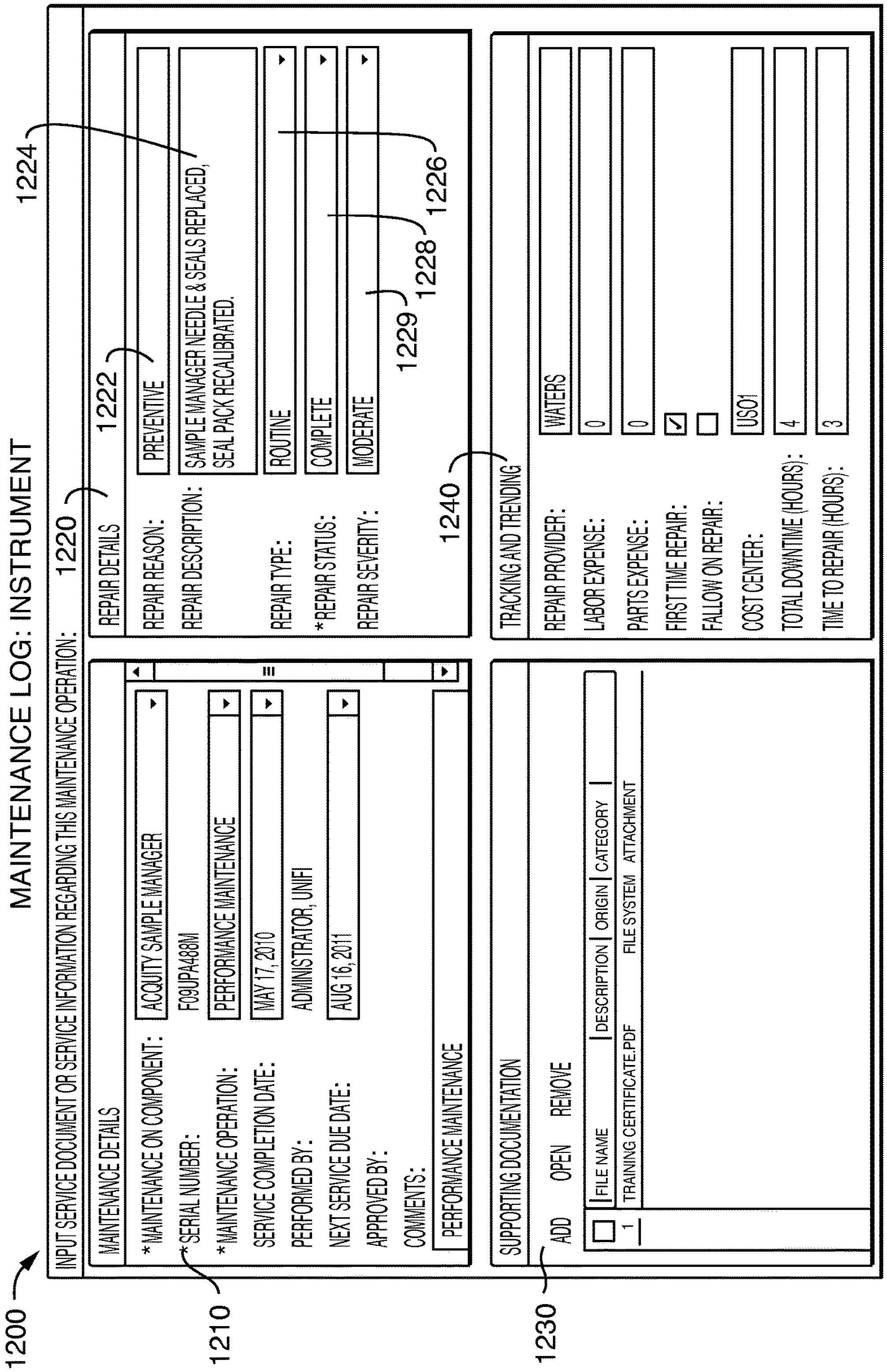

FIG. 14

MAINTENANCE LOG: COMPUTER

INPUT SERVICE DOCUMENT OR SERVICE INFORMATION REGARDING THIS MAINTENANCE OPERATION:

MAINTENANCE DETAILS — 1610

- *MAINTENANCE ON COMPONENT: HARDWARE
- *SERIAL NUMBER:
- *MAINTENANCE OPERATION: ADDED MEMORY
- SERVICE COMPLETION DATE: MAY 17, 2010
- PERFORMED BY: ADMINISTRATOR, UNIFI
- NEXT SERVICE DUE DATE: JUN 1, 2010
- APPROVED BY:
- COMMENTS: I ADDED 4 GB OF RAM IN ADVANCE OF NEW SOFTWARE ROLLOUT FOR THIS PC

REPAIR DETAILS — 1620

- REPAIR REASON: PLANNED UPGRADE
- REPAIR DESCRIPTION: INSTALLED MEMORY DIMM SLOTS 2 & 4
- REPAIR TYPE: NON-ROUTINE
- *REPAIR STATUS: COMPLETE
- REPAIR SEVERITY: MINOR — 1622

1640

TRACKING AND TRENDING

- REPAIR PROVIDER: IT
- LABOR EXPENSE: 0
- PARTS EXPENSE: 0
- FIRST TIME REPAIR: ☑
- FALLOW ON REPAIR: ☐
- COST CENTER: US01
- TOTAL DOWNTIME (HOURS): 2
- TIME TO REPAIR (HOURS): 1

SUPPORTING DOCUMENTATION — 1630

ADD  OPEN  REMOVE

| FILE NAME | DESCRIPTION | ORIGIN | CATEGORY |

☐ 1

1600

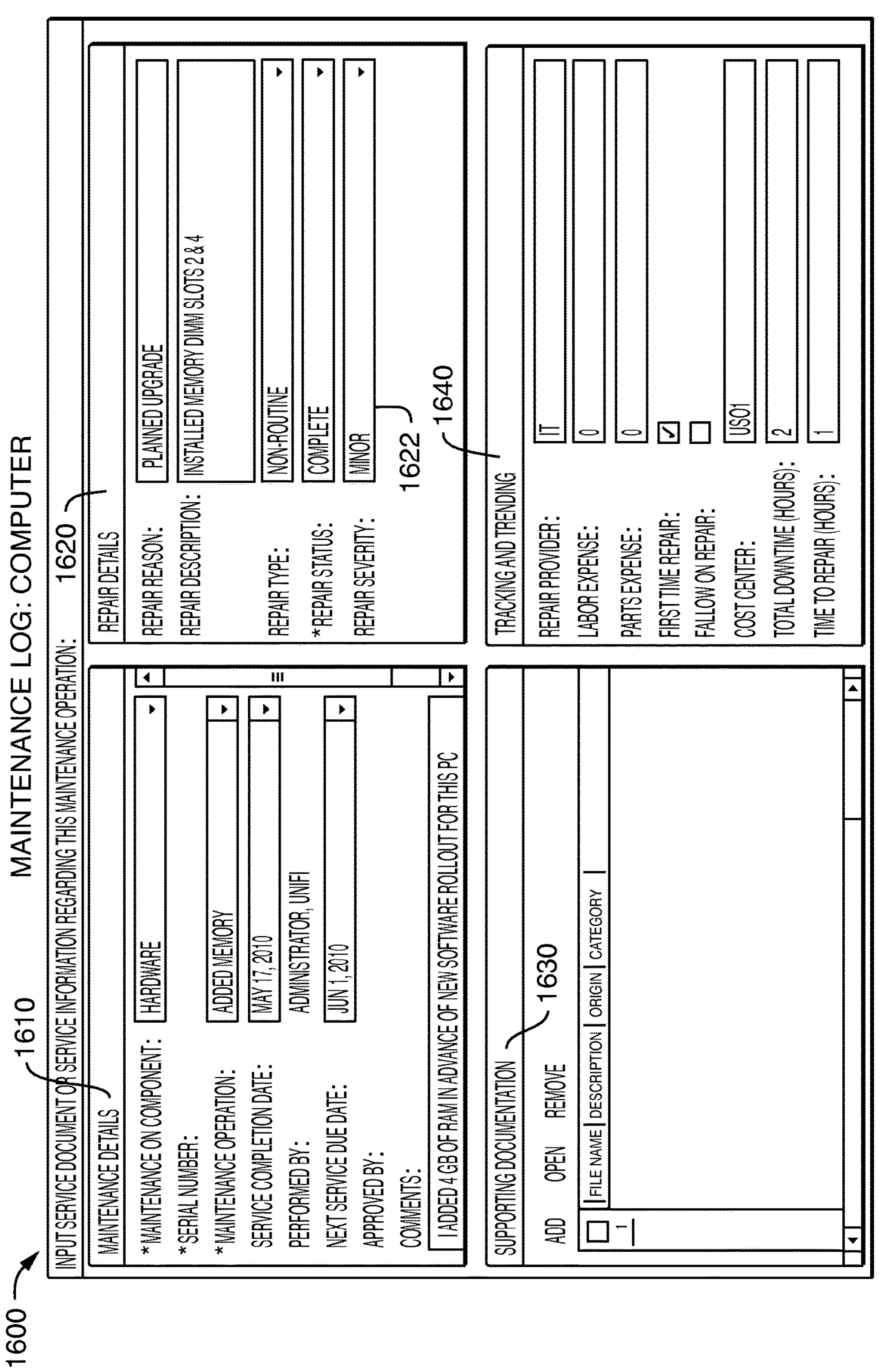

FIG. 18

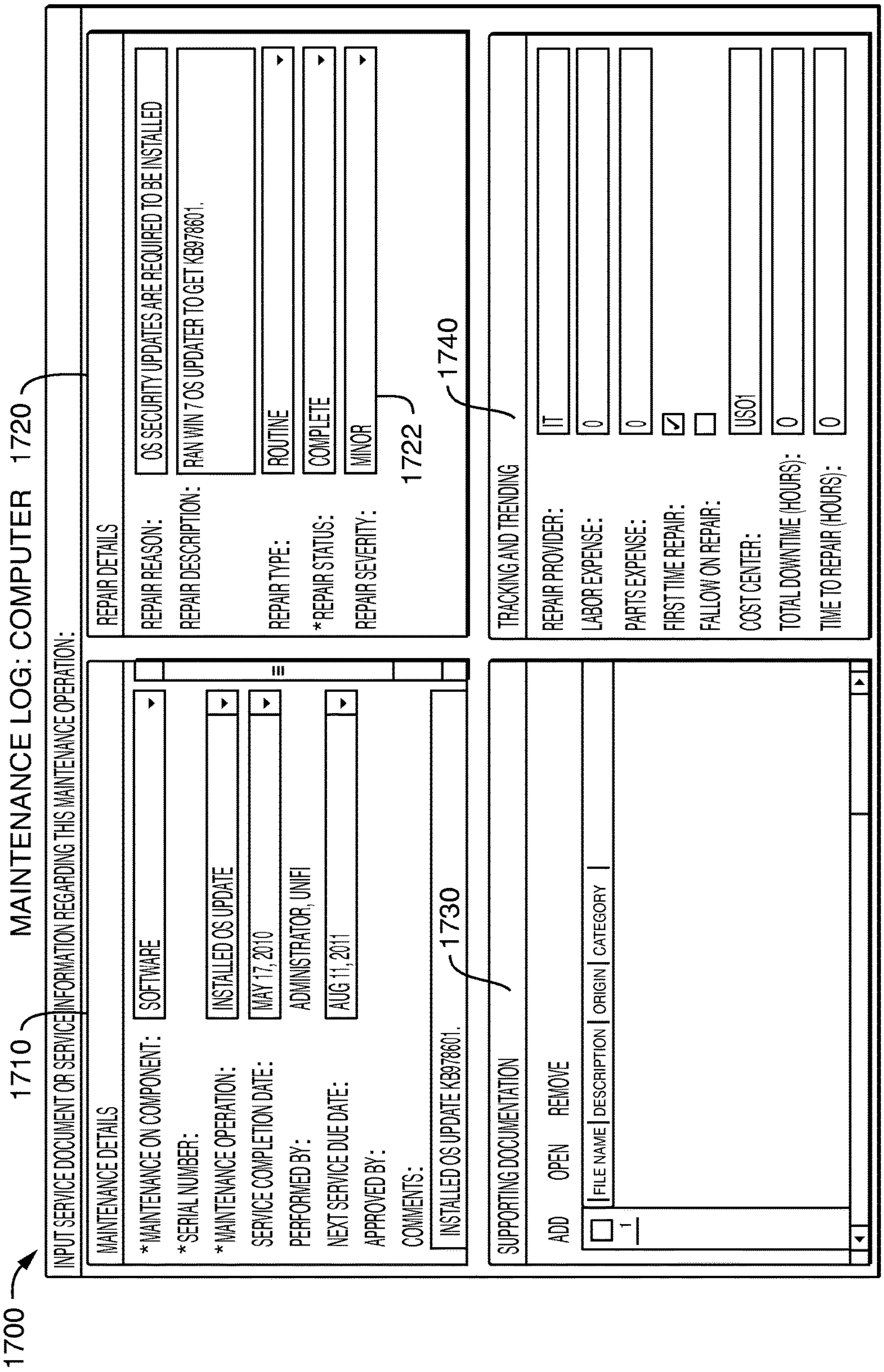

FIG. 19

MAINTENANCE LOG: COMPUTER 1720

INPUT SERVICE DOCUMENT OR SERVICE INFORMATION REGARDING THIS MAINTENANCE OPERATION:

MAINTENANCE DETAILS — 1710

- *MAINTENANCE ON COMPONENT: SOFTWARE
- *SERIAL NUMBER:
- *MAINTENANCE OPERATION: INSTALLED OS UPDATE
- SERVICE COMPLETION DATE: MAY 17, 2010
- PERFORMED BY: ADMINISTRATOR, UNIFI
- NEXT SERVICE DUE DATE: AUG 11, 2011
- APPROVED BY:
- COMMENTS: INSTALLED OS UPDATE KB978601.

REPAIR DETAILS

- REPAIR REASON: OS SECURITY UPDATES ARE REQUIRED TO BE INSTALLED
- REPAIR DESCRIPTION: RAN WIN 7 OS UPDATER TO GET KB978601.
- REPAIR TYPE: ROUTINE
- *REPAIR STATUS: COMPLETE
- REPAIR SEVERITY: MINOR

1722

SUPPORTING DOCUMENTATION — 1730

ADD   OPEN   REMOVE

| FILE NAME | DESCRIPTION | ORIGIN | CATEGORY |

TRACKING AND TRENDING — 1740

- REPAIR PROVIDER: IT
- LABOR EXPENSE: 0
- PARTS EXPENSE: 0
- FIRST TIME REPAIR: ☑
- FALLOW ON REPAIR: ☐
- COST CENTER: US01
- TOTAL DOWNTIME (HOURS): 0
- TIME TO REPAIR (HOURS): 0

1700

TECHNIQUES FOR QUALIFICATION AND MAINTENANCE OF SCIENTIFIC INFORMATION SYSTEM DEVICES

CROSS REFERENCE TO RELATED APPLICATIONS

This application is a National Stage of International Application No. PCT/US2012/042194, filed Jun. 13, 2012, TECHNIQUES FOR QUALIFICATION AND MAINTENANCE OF SCIENTIFIC INFORMATION SYSTEM DEVICES, which claims priority to U.S. Provisional Application No. 61/497,104, filed Jun. 15, 2011, TECHNIQUES FOR QUALIFICATION AND MAINTENANCE OF SCIENTIFIC INFORMATION SYSTEM DEVICES, all of which are incorporated by reference herein.

BACKGROUND

Technical Field

This application generally relates to computer systems data systems and/or other system devices, and more particularly to techniques used in connection with qualification, verification, calibration, validation and maintenance of such devices.

Description of Related Art

Different scientific instruments may be included in a laboratory. Such scientific instruments may include mass spectrometers (MS), instruments performing a chromatographic separation such as gas chromatographs (GC) and liquid chromatographs (LC), and the like. Operation of such instruments may be controlled using a computer system directly connected to one or more of the instruments. For example, a computer system may be used to control operation of an LC and an MS to obtain mass spectral data for a sample. The computer system may also be used in connection with performing further processing and analysis of the data, such as the mass spectra, acquired using the instruments. The data acquired from the instruments (such as raw data acquired from the instruments prior to subsequent analysis processing) as well as additional data analysis information may be stored on data storage devices of the computer system. Users may log on to the computer system with account names and passwords for authentication. Such authentication may be required prior to allowing a user to operate the instruments and also utilize software on the computer system to perform subsequent data processing and analysis of the data acquired using the instruments.

The foregoing system including the instruments and computer may be used to analyze various products and samples such as, for example, in connection with products developed by pharmaceutical companies and testing samples in hospitals and governmental laboratories. The systems performing this analysis may be regulated and required to be compliant with certain standards, guidelines, and/or regulations covering a wide variety of items. For example, the use of scientific instruments may be required to comply with government regulations for instrument qualification and validation for the same throughout the lifecycle of such instruments and other devices in a system.

SUMMARY OF THE INVENTION

In accordance with one aspect of the invention is a method for determining a qualification status of a device in a system comprising: determining an occurrence of a trigger event for the device, said trigger event being caused by an occurrence of any of a trend-based event, time-based event, a performance-based event, a usage-based event, and an unscheduled event; providing user notification to perform a first action responsive to said occurrence, said first action being an action to perform any of a maintenance activity, a repair activity, and a test for the device; and updating the qualification status of the device in accordance with said first action. The first action may be a maintenance activity or a repair activity. The method may include creating a log including information regarding the maintenance or repair activity, the log including requalification criteria used in determining whether requalification is needed responsive to performing the maintenance or repair activity, said requalification criteria including a severity associated with the maintenance or repair activity; and determining, in accordance with said requalification criteria, whether to set the qualification status of said device to unqualified. It may be determined to set the qualification status of the device to unqualified. The method may also include updating a user interface element to indicate the device having an unqualified status. The maintenance activity or repair activity may be linked to a qualification procedure used for performing one or more qualification tests for the device. The method may also include performing testing using the qualification procedure; and updating the qualification status of the device in accordance with results of performing the testing using the qualification procedure. The method may include determining, in accordance with said requalification criteria, whether to disable the device from further use until one or more subsequent confirmatory actions are successfully performed. The one or more qualification records are automatically created for one or more qualification tests performed using the qualification procedure. A next qualification date may be automatically determined in response to successfully performing the one or more qualification tests. The first action may be a maintenance action, and the log may include information indicating whether the maintenance action has been completed. The next maintenance date may be automatically determined in response to indicating in said log that the maintenance action has been completed. The test may be a qualification test for the device. The method may also include determining, in accordance with said requalification criteria, whether to set the qualification status of the device to not qualified until one or more subsequent confirmatory actions are successfully performed. The one or more subsequent confirmatory actions may include performing a qualification test for the device. The device may be included in a regulated system operating in accordance with regulatory requirements. The device may be a scientific laboratory instrument. The device may be a scientific laboratory instrument that performs any of liquid chromatography, gas chromatography, mass spectrometry, supercritical fluid chromatography, capillary electrophoresis, and analog to digital signal conversion and/or transmission. The device may be a computer system. An occurrence of a time-based event may be a planned or scheduled event that depends on an amount of lapsed calendar time. An occurrence of a usage-based event may be a planned or scheduled event that depends on an amount of actual usage of the device, component of the device and/or part of the component. An occurrence of a performance-based event depends on whether the device meets specified performance criteria. An occurrence of an unscheduled event for the device may be an unscheduled repair, unscheduled update, or unscheduled upgrade. An observed trend over a time period regarding an amount of downtime may be used in determining the occurrence of the unscheduled event to perform the unscheduled repair. An observed trend over a time period regarding analytical results generated by the device may be used in determining the occurrence of the unscheduled event to perform the unscheduled repair. The first action may be a maintenance activity to replace the device with a new device, new component comprising the device, or new part comprising a component of the device.

In accordance with another aspect of the invention is a system comprising a plurality of scientific instruments, one or more computer systems used to control and/or communicate with the plurality of scientific instruments and a computer readable medium. The computer readable medium comprises code stored thereon for determining an occurrence of a trigger event for a device, said device being any of the plurality of scientific instruments and the one or more computer systems, said trigger event being caused by an occurrence of any of a time-based event, a performance-based event, a trend-based event, a usage-based event, and an unscheduled event; providing user notification to perform a first action responsive to said occurrence, said first action being an action to perform any of a maintenance activity, a repair activity, and a test for the device; and updating a qualification status of the device in accordance with said first action.

In accordance with another aspect of the invention is a computer readable medium comprising code stored thereon for determining a qualification status of a device in a system, the computer readable medium comprising code stored thereon for: determining an occurrence of a trigger event for the device, said trigger event being caused by an occurrence of any of a time-based event, a performance-based event, a usage-based event, a trend-based event, and an unscheduled event; providing user notification to perform a first action responsive to said occurrence, said first action being an action to perform any of a maintenance activity, a repair activity, and a test for the device; and updating the qualification status of the device in accordance with said first action.

In accordance with yet another aspect of the invention is a system comprising a plurality of scientific instruments, one or more computer systems used to control and/or communicate with the plurality of scientific instruments, and a computer readable medium. The computer readable medium comprises code stored thereon for determining an occurrence of a trigger event for a device, said device being any of the plurality of scientific instruments and the one or more computer systems, said trigger event being caused by an occurrence of any of a time-based event, a performance-based event, a trend-based event, a usage-based event, and an unscheduled event; providing user notification to perform a first action responsive to said occurrence, said first action being an action to perform any of a maintenance activity, a repair activity, and a test for the device; and updating a compliance status of the device in accordance with said first action. The compliance status may be determined in accordance with compliance with any one or more of a qualification requirement, a verification requirement, a validation requirement, and a calibration requirement. The first action may be to perform a maintenance or repair activity and the compliance status may be set to not compliant after performing the maintenance or repair activity until one or more subsequent confirmatory actions are successfully performed. The one or more subsequent confirmatory actions include performing any one or more of a qualification test, a verification test, a validation test and a calibration test for the device. The test for the device may be any of a qualification test, a verification test, a validation test and a calibration test for the device.

BRIEF DESCRIPTION OF THE DRAWINGS

Features and advantages of the present invention will become more apparent from the following detailed description of exemplary embodiments thereof taken in conjunction with the accompanying drawings in which:

FIGS. 4-19 are examples of user interface displays that may be used in an embodiment in accordance with techniques herein;

DETAILED DESCRIPTION OF EMBODIMENT(S)

Figure 1:
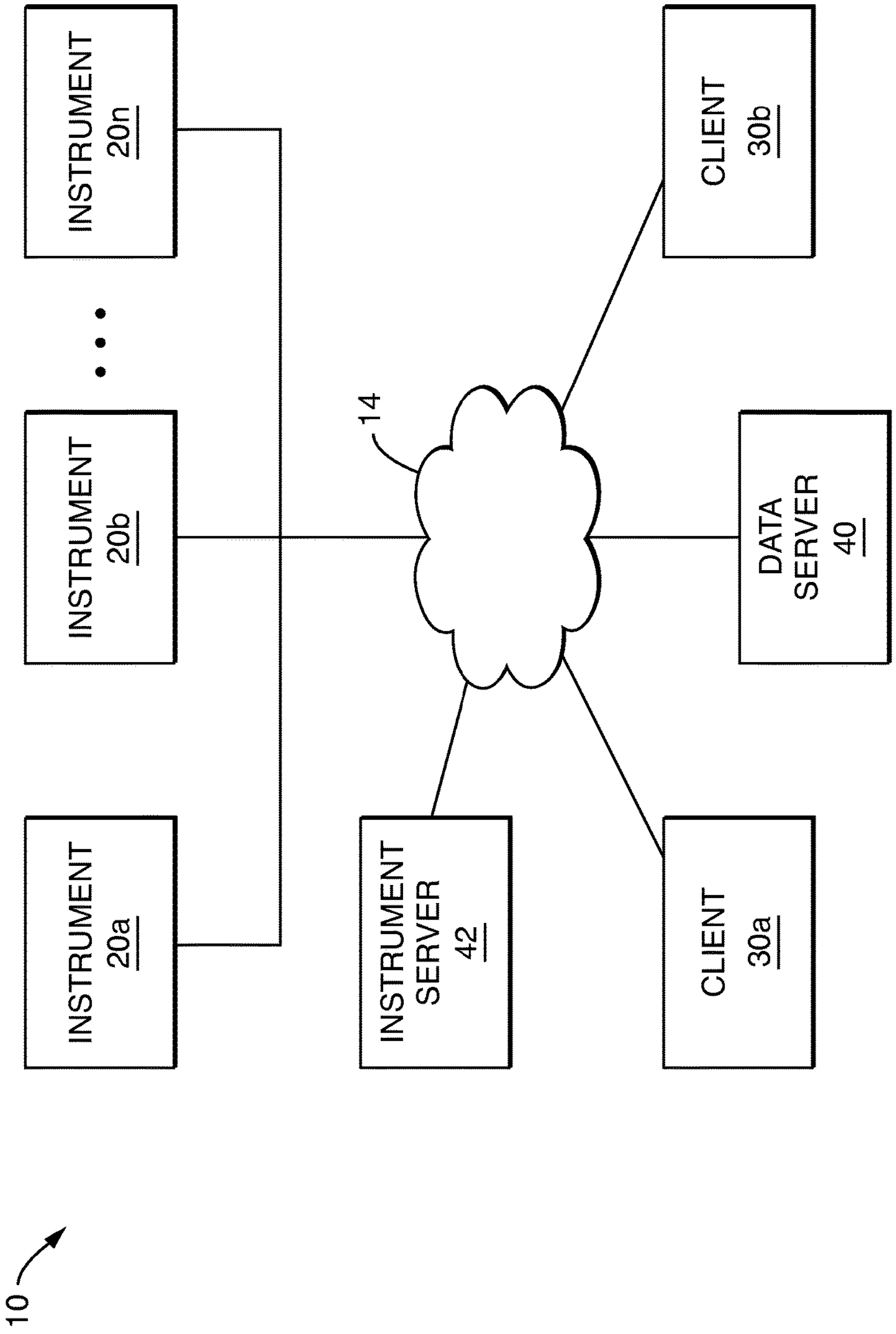
FIGS. 1 and 2A are examples of embodiments of a system that may utilize the techniques described herein.

Referring to FIG. 1, shown is an example of an embodiment of a computing environment and system that may be used in performing the techniques described herein. The computing environment illustrated in FIG. 1 is only one example of a suitable computing environment and is not intended to suggest any limitation as to the scope of use or functionality of the techniques described herein. Those skilled in the art will appreciate that the techniques described herein may be suitable for use with other general purpose and specialized purpose computing environments and configurations. Examples of well known computing systems, environments, and/or configurations include, but are not limited to, personal computers, server computers, hand-held or laptop devices, multiprocessor systems, microprocessor-based systems, programmable consumer electronics, network PCs, minicomputers, mainframe computers, virtualized computing environments (e.g., such as using virtual machines executing in a virtualized environment. For example, an embodiment may have one or more virtual machines executing on a single physical machine in a virtualized environment using virtualization software produced by VMware, Inc.), distributed computing environments that include any of the above systems or devices, and the like.

The techniques set forth herein may be described in the general context of computer-executable instructions, such as program modules, executed by one or more computers or other devices. Generally, program modules include routines, programs, objects, components, data structures, and the like, that perform particular tasks or implement particular abstract data types. Typically the functionality of the program modules may be combined or distributed as desired in various embodiments.

Included in FIG. 1 are instruments 20*a*-20*n*, client computers 30*a*, 30*b*, data server computer 40, instrument server computer 42, and a network 14. Each of the client computers 30*a*, 30*b* and server computers 40, 42 may be a standard, commercially-available computer or a special-purpose computer that may be used to execute one or more program modules. Described in more detail elsewhere herein are program modules that may be executed by client computers 30*a*, 30*b* and/or server computers 40,42 in connection with facilitating processes and practices in connection with qualification and maintenance of devices of FIG. 1. Such qualification and maintenance may relate to any aspect of the system and its components such as, for example, qualification and maintenance of the instruments 20*a*-20*n* and servers 40,42, software applications and data files stored on the data server, and the like, as may occur throughout the lifecycle of the system and components thereof. In one embodiment as described in more detail below, functionality for performing qualification and maintenance may be provided by software included in a data system used in connection with components of the illustrated system such as the instruments 20*a*-20*n* and clients 30*a*, 30*b*.

The computers 30*a*, 30*b*, 40 and 42 may operate in a networked environment and communicate with other computers, instruments, and other devices not shown in FIG. 1. The instruments 20*a*-20*n* may be scientific instruments such as liquid chromatography systems, supercritical fluid chromatography systems, capillary electrophoresis, gas chromatography systems, mass spectrometers, and other instrumentation types which may perform, for example, analog to digital signal conversion and/or transmission which are connected to the network 14 and in communication with the client computers 30*a*, 30*b* and server computers 40,42. The instruments 20*a*-20*n* may include, for example, one or more scientific instruments offered by Waters Corporation of Milford, Mass. (or any other supplier). These may also be non-networked devices such as pipettes, balances, calipers, voltmeters, pH meters or a wide variety of other devices.

As will be apparent to those of ordinary skill in the art, the techniques described herein may also be used in an embodiment in which a computer is not connected to a network. For example, a computer system utilizing the techniques herein may be directly connected to one or more instruments rather than through a network. For purposes of illustration, exemplary embodiments may be described which relate to computers used with instruments, such as scientific instruments, but should not be construed as so limited. The foregoing and other aspects and uses of techniques herein are described in more detail in following paragraphs.

The client computers 30*a*, 30*b* and server computers 40, 42 may have one or more applications executing thereon for use in connection with the instruments 20*a*-20*n*. In one embodiment, the data system may be the UNIFI™ Scientific Information System from Waters Corporation of Milford, Mass. The techniques described herein for qualification and maintenance may be embodied in software included in such a data system which may also provide other functionality. For example, the data system may provide functionality to collect, process, and distribute scientific information. With the data system, laboratories are able to automatically capture, secure, access, and disseminate information from any analytical technology. The data system may include functionality for an automated electronic repository that stores and manages all types of scientific data to a centralized database, offering integration with a multitude of research applications. The data system may be used in connection with controlling and managing the instruments, providing security by controlling access to activities within the data system, as well as the data and devices (e.g., instruments and computers) on the system, performing data processing, designing and using methods for data analyses and reporting, and the like. For example, the data system may include a database and may be used to provide a data-secured environment to store and retrieve data in support of regulated laboratories, using an embedded, relational database, acquire data, perform calculations, generate reports, and control a variety of instruments, perform instrument and/or software qualification, validation, and the like. An example of data that may be acquired from one of the instruments 20*a*-20*n*, where the instrument is a mass spectrometer, is a series of spectra or scans collected over time. As known in the art, a mass-to-charge spectrum is intensity plotted as a function of m/z. Each element, a single mass-to-charge ratio, of a spectrum may be referred to as a channel. Viewing a single channel over time provides a chromatogram for the corresponding mass-to-charge ratio. The generated mass-to-charge spectra or scans can be acquired and recorded on a storage medium such as a hard-disk drive or other storage media accessible to a computer. Typically, a spectrum or chromatogram is recorded as an array of values and may be stored, for example, in a database of the data system on the data server 40. The spectra stored on the data server 40 may be accessed using one of the client computers 30*a*, 30*b* such as for display, subsequent analysis (such as in connection with performance qualification or PQ described elsewhere herein), and the like. Data such as the foregoing may be stored in a data container or repository, such as a relational database or other storage facility, and remotely shared such as by multiple clients. As another example, the data system may be used in connection with providing settings for the instruments 20*a*-20*n*. For example, the data system may be used in connection with setting various parameters of a mass spectrometer and liquid chromatography system and ensuring proper access and control in connection with modifying such settings. The instrument server 42 may communicate with the one or more instruments 20*a*-20*n* to control the setting and operation of such instruments. A user may access instruments 20-20*n* or data such as may be stored on the data server 40 by logging onto the data system using one of the clients 30*a*, 30*b*. The data server 40 may include software of the data system for controlling access to the system using authentication techniques known in the art such as user account and passwords with one or more roles associated with the user accounts. As a security measure, roles may define types of data access and operations which an associated user is allowed to perform.

Described in following paragraphs are techniques that may be used in connection with providing software that may be included in the data system for use in connection with techniques described herein for qualification, verification, validation, calibration, and maintenance operations for devices of the system. The techniques may be used to provide for qualification and maintenance of devices and components comprising such devices and may embody recommended processes and practices for the systematic risk-based management of compliant regulated systems and the analytical instruments, computer systems and possibly other devices thereof throughout their respective lifecycles. Described herein are techniques that may be used to centralize, proceduralize and standardize the maintenance and management of regulated systems and associated compliance records in accordance with regulations and standards of such systems. As examples, the techniques herein may be used in connection with systems providing pharmaceuticals, biopharmaceuticals, medical devices, conducting clinical trials, running certified laboratories, and the like. Systems used in connection with the foregoing may require ensuring the validity and integrity of data and results and proving compliance with applicable standards and regulations. As will be described below, the techniques herein for qualification and maintenance may be used in connection with systems including instruments and components performing such applications and uses.

It will be appreciated by those skilled in the art that although devices of the system of FIG. 1 are shown in the example as communicating in a networked environment, the devices may communicate with each other and/or other devices utilizing different communication mediums and may or may not be networked together. For example, the devices of FIG. 1 may communicate with each other and/or one or more devices utilizing a network connection, and/or other type of link known in the art including, but not limited to, the Internet, an intranet, or other wireless and/or hardwired connection(s). Furthermore, as noted above, the techniques herein may be used in an embodiment with standalone computers connected directly to instruments such as without network connectivity.

Figure 2:
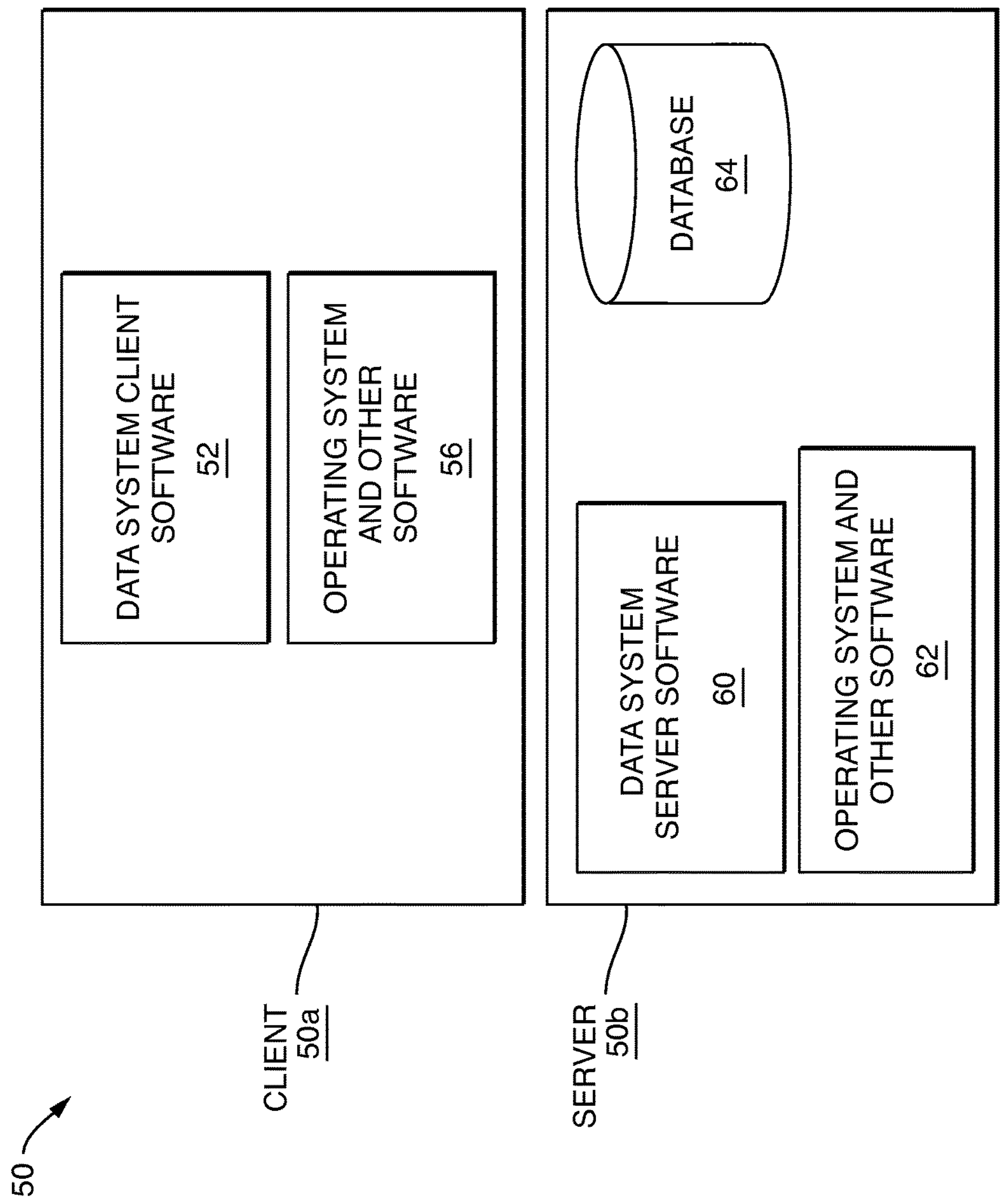
FIG. 2 is an example of components that may be included in a client and a server in an embodiment in accordance with techniques herein.

Referring to FIG. 2, shown is an example of components that may be included in a client computer 20*a* and data server computer 40 in an embodiment in accordance with techniques herein. The client computer 20*a* may include data system client software 52 and operating system and other software 56. The data system client software 52 may be, for example, the client portion of the data system described above to control and manage the instruments. In one embodiment, the client may be characterized as a thin client or a fat client. With the thin client, a majority of the application's functionality is performed by software included on the data server 40. In contrast, a thick or fat client is one in which a large portion of the application's functionality is performed by or embodied in the client software 52. The particular partitioning of functions performed by the client and data server may vary with application. Element 56 represents the operating system and possibly other software that may be on the client computer 20*a*. The operating system may be any one of a variety of commercially available or proprietary operating system such as, for example, a Windows-based operating system by Microsoft Corporation.

Figure 2A:
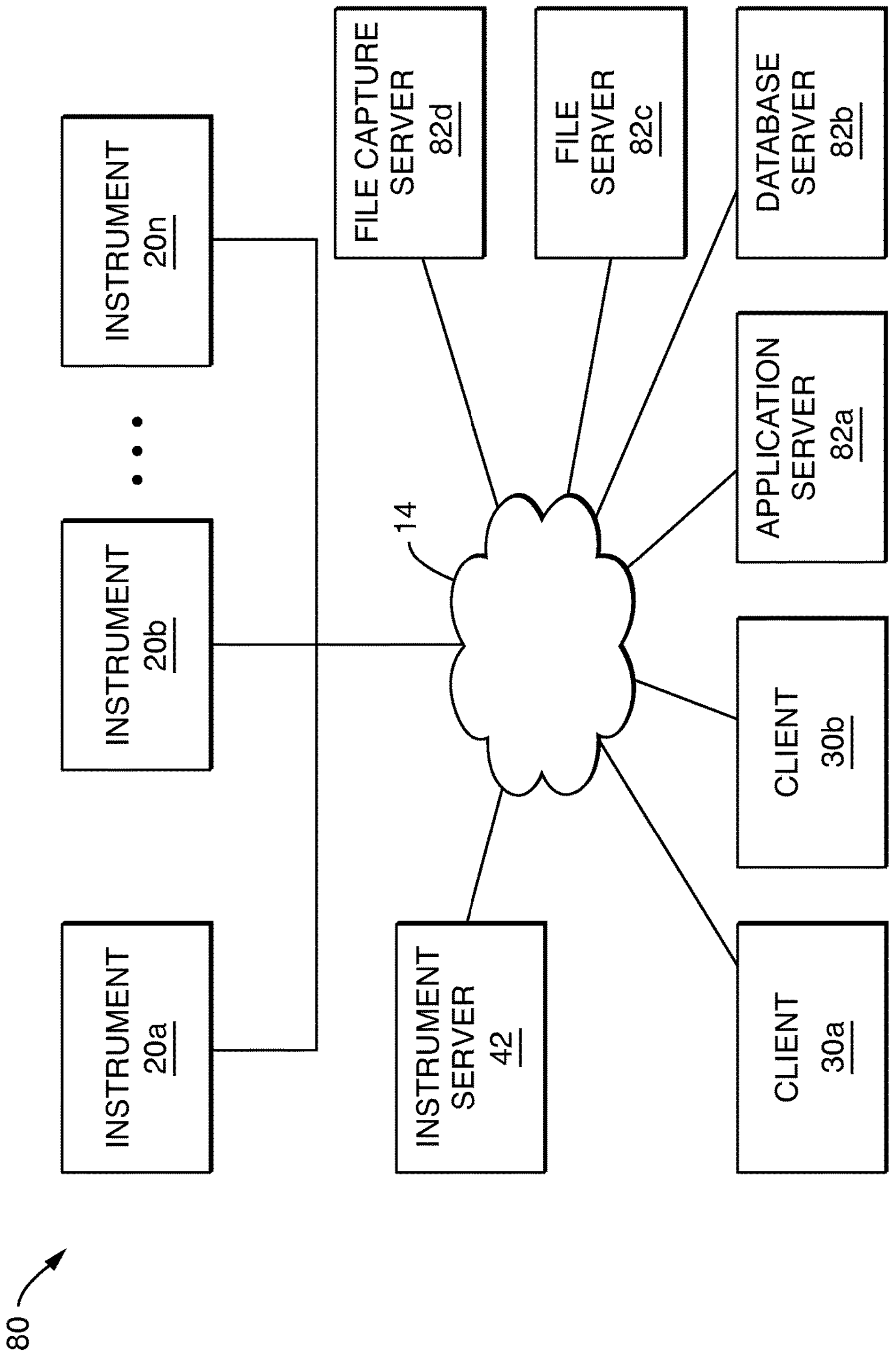

The data server 40 may include data system server software 60, a database 64, and operating system and other software 62. In some embodiments, the data server may also be distributed such that its functionality is partitioned and performed by multiple servers rather than a single server such as illustrated in FIG. 1. For example, with reference to FIG. 2A, rather than have a single data server 40 as in FIG. 1, an embodiment may have multiple servers such as, for example, a database server 82*b*, an application server 82*a*, a file server 82*c*, a file capture server 82*d*, and the like. Each of the foregoing multiple servers may perform a particular portion of the overall functionality of the single data server 40 of FIG. 1.

Referring again to FIG. 2, software represented by elements 60 and 64 may be included in the data system. The software 60 may include software implementing techniques described herein for qualification and maintenance of devices including instruments and computers of the system. This is described in more detail in following paragraphs.

Although not illustrated in FIG. 2, each of the client 20*a* and data servers 40 may be a computer include one or more processing units, memory, a network interface unit, storage, and the like. Depending on the configuration and type of computer, the memory thereof may be volatile (such as RAM), non-volatile (such as ROM, flash memory, etc.) or some combination of the two. The storage may include removable and/or non-removable storage for use with computer system including, but not limited to, USB devices, magnetic or optical disks, or tape. Such storage devices have associated computer-readable media that may be utilized by the computer and may include, for example, a hard disk or CD-ROM drive, that can be accessed by the computer. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, (DVD) or other optical storage, magnetic cassettes, magnetic tape, magnetic disk storage or other magnetic storage devices, or any other medium which can be used to store the desired information and which can accessed by the computer. Each of the computers may also contain communications connection(s) to facilitate communication with other devices and components such as, by way of example, input devices and output devices. Input devices may include, for example, a keyboard, mouse, pen, voice input device, touch input device, barcode reader, etc. Output device(s) may include, for example, a display, speakers, printer, and the like. These and other devices are well known in the art.

As mentioned above, the data system client software 52 as well as server software 60 and the database 64 may comprise a data system of one or more applications used in connection with the instruments of FIG. 1. For example, such software represented by element 60 may be used to control operations of a liquid chromatography system or mass spectrometer, set instrument parameters used to operate the instruments, collect and store data such as results of analysis performed by the instruments, and the like. The software included in the data system may be used to manage system security of the instruments, securely provide for storing data that is used and generated by the instruments, control access to such data and the actions within the application with respect to users in accordance with roles, permissions, and the like.

The qualification and maintenance techniques described herein may be used in a regulated as well as a non-regulated system. For example, the techniques herein may be used in connection with a regulated system meeting FDA regulatory requirements such as specified in 21 CFR parts 211, 11, 820 and many others. In one embodiment as described herein, the techniques may provide for initiation and management of qualification and maintenance activities, records, and the like, such as through use of a centralized user interface console. Functionality provided may include, for example, organizing tasks, protocols and records (such as qualification and maintenance records) and associating them with particular instruments and computers. Systems and components thereof may have a defined lifecycle within which their commissioning, compliance status, use, maintenance and decommissioning is traceable and supporting records associated with each particular system. Controls may be utilized such that the compliance state of the system and components may be assured prior to allowing performance of particular analysis or other uses of the system and/or components. Qualification and maintenance records may be linked so that maintenance tasks and subsequent requalification tests are logically associated. A severity may be associated with a maintenance task and may dictate the level or necessity of performing confirmatory testing and/or other actions to return the system to production use. Events and statuses which may pose a compliance issue may be flagged to provide user notification. Management information related to the maintenance and other aspects of the system and components may be tracked where such information may be further used, for example, in connection with tracking and trending.

In connection with instrument or computer system qualification, verification activities may include, for example, documenting or providing objective evidence regarding performance of qualification processing (e.g., tests performed in connection with installation qualification (IQ), operational qualification (OQ) and/or performance qualification (PQ)), commissioning, and the like. As will be described below, an embodiment in accordance with techniques herein may be used with qualification and maintenance activities, records, and the like, for devices. The embodiment may also optionally include other functionality such as related to verification activities, records, and the like.

In accordance with some systems and uses that may include providing qualification in connection with software, software verification may be generally characterized as by ISO and ASTM as confirmation, through the provision of objective evidence that specified requirements related to such qualifications have been fulfilled and a systematic approach to verify that manufacturing systems, acting singly or in combination, are fit for intended use, have been properly installed, and are operating correctly. The foregoing is an "umbrella" term that encompasses all types of approaches to assuring systems are fit for use such as qualification, commissioning and qualification, verification, system validation, or other.

In accordance with other systems and uses, software verification may be characterized as defined by the FDA in the context of its guidance *General Principles of Software Validation* (applicable within the medical device context). In this case, software verification may be characterized as providing objective evidence that the design outputs of a particular phase of the software development life cycle meet all of the specified requirements for that phase. Software verification looks for consistency, completeness, and correctness of the software and its supporting documentation, as it is being developed, and provides support for a subsequent conclusion that software is validated. Software testing is one of many verification activities intended to confirm that software development output meets its input requirements. Other verification activities include various static and dynamic analyses, code and document inspections, walkthroughs, and other techniques. Software validation is specifically defined by the FDA within its guidance for the validation of software within the medical device context as "confirmation by examination and provision of objective evidence that software specifications conform to user needs and intended uses, and that the particular requirements implemented through software can be consistently fulfilled."

Qualification may be generally be described as an action of proving and documenting that equipment or ancillary systems are properly installed, work correctly, and actually lead to the manufacturer's expected results. Qualification can be a subset of validation, but the individual qualification steps alone may not satisfy the validation requirement of establishing fit for intended use. Validation may be described as confirmation by examination and provision of objective evidence that the particular requirement for a specific intended use can be consistently fulfilled. In this case, processing is performed to validate the proper functionality of specific software operational features by automatically exercising those features in the software and collecting objective evidence of the result, effect or output.

Installation qualification (IQ) is defined by the FDA in their glossary of computer systems software development terminology glossary as establishing confidence that process equipment and ancillary systems are compliant with appropriate codes and approved design intentions, and that manufacturer's recommendations are suitably considered. More generally in connection with IQ, processing may be performed to log and record information for verifying and/or documenting that a computerized system, instrument, and the like, is installed according to written and pre-approved specifications. As an example for a chromatography system or instrument, IQ establishes that the system is received as designed, is installed properly, and verifies where the system is installed is appropriate according to the manufacturer's specifications.

Operational qualification (OQ) is defined by the FDA in their glossary of computer systems software development terminology glossary as establishing confidence that process equipment and sub-systems are capable of consistently operating within established limits and tolerances. More generally in connection with OQ, processing may be performed to log and record information for verifying and/or documenting that a computerized system, instrument and the like, operates according to written and pre-approved specifications. For example, OQ for a scientific or analytical instrument may include performing testing to ensure that the instrument operates throughout specified operating ranges. Information regarding performance, results, and the like, of tests for OQ may be recorded. As an example for a chromatography system or instrument, OQ ensures that key components or primary functionality thereof is operational according to operational specifications in the selected environment which may include its role within an integrated system. As another example, OQ for a computer system may be performed to verify calculation and reporting functionality. For example, processing a known benchmarked data set and confirming that the installed application generates equivalent results and issues equivalent reports. As an additional example, OQ for a computer system may be performed to verify security functionality facilitating compliance with 21 CFR Part 11 electronic records and signature regulation requirements. The results and outputs of such tests collected as documented evidence of correct operation of this functionality within the specific environment of the deployment for OQ of the computer system.

Performance qualification (PQ) (such as a Chromatography Data System or like data collection and/or organization system) may be defined as establishing documented evidence through appropriate testing and collection of objective evidence that the processes carried out by the integrated computerized system consistently perform as expected for the intended use. For example, PQ may verify that all components of an instrument, such as a mass spectrometer, perform properly when all components thereof are integrated. For example, PQ for an instrument may include performing tests and documenting such results to verify that an instrument is capable of performing or controlling the activities of a process the instruments is required to perform, according to written and pre-approved specifications, while in its specified operating environment. Performance testing of an instrument may be performed, for example, to demonstrate the accuracy and precision of the instrument. For example, performance testing of a liquid chromatograph or mass spectrometer may include examining results or output generated as a result of performing an injection, run or experiment using the instrument.

Qualification of instruments, or instrument systems, is described in more detail, for example, in U.S. Pat. No. 6,456,955, Andrews et al. Automated Test Protocol, Issued Sep. 24, 2002, which is incorporated by reference herein.

The foregoing, as well as other exemplary uses of the techniques herein, are described in more detail in following paragraphs and figures.

Figure 3:
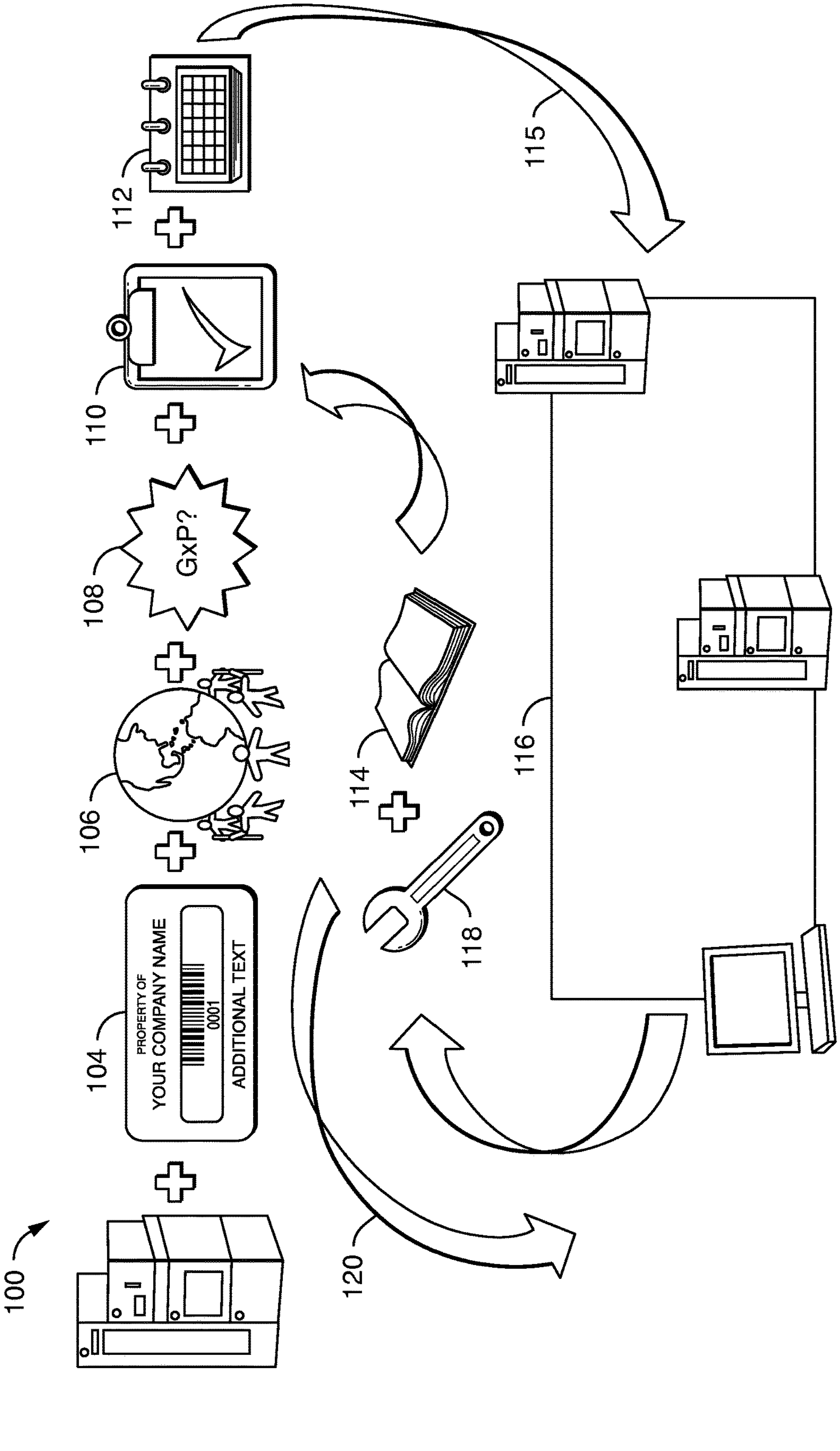
FIG. 3 is an example illustrating a lifecycle of a device such as an instrument or computer system in an embodiment in accordance with techniques herein.

Referring to FIG. 3, shown is an example illustrating an exemplary lifecycle of a system, such as an instrument or computer system as may be included in an embodiment utilizing the techniques herein. As part of commissioning or putting into use an instrumentation system or computer 102, the instrument or computer may be assigned an asset id 104. Element 106 illustrates that it may be decided as to where the instrument or computer may is physically located (e.g., geographically) and whether element 102 will be a regulated system (e.g., subject to system/government and/or standards/regulations). The instrument or computer may then be qualified 110 and schedules may be set 112 for future qualification and/or maintenance. The instrument or computer 102 may then be placed into production use such as in a laboratory or other system as illustrated in FIG. 1. One or more types of events may occur at various points during the lifecycle of the instrument or computer. Such event may include, for example planned or scheduled events as well as unplanned or unscheduled events. Planned or scheduled events may include, for example, scheduled maintenance activities. Unplanned or unscheduled events may include, for example, a repair or other unplanned activity. Events can generally be categorized as being triggered by usage limits, performance limits, trend limits, repairs (or other unplanned activity), or time limits. The occurrence of any such event may trigger or result in an event notification 115 such as to a user. The user may then monitor or examine 116 the instrument or computer in response to the occurrence of such an event. In response to the event occurrence, any one or more different actions may be performed. Such actions may include, for example, performing a maintenance or repair activity 118 and then logging 114 such activity. Depending on the particular activity of 118, requalification 110 (as well as other confirmatory actions) may be performed and/or updates may be made 112 to the next scheduled repair or qualification. As a variation to the foregoing of exemplary responsive actions in response to the event occurrence, maintenance and/or repair 118 may not be required responsive to an event occurrence. Rather, processing may continue directly with performing requalification. For example, for an instrument 102, requalification may be performed after a particular number of uses, after a certain time period has lapsed, and the like, and may not require any maintenance or repair activity. Rather, all that may be needed is to perform the qualification tests as illustrated by 110. In an embodiment of a system using the techniques herein, records may be maintained for qualification and maintenance activities of the instrument and computer. The foregoing illustrated cyclic process of 110, 112, 116, 118 and 114 (where 118 and 114 may be optionally performed as needed based on the particular point in time and event occurrence) may be performed repeatedly during the lifetime of the instrument or computer 102. At the user's discretion or after a certain time period, age or usage limit, device support date, and the like, the instrument or computer 102 may be decommissioned (e.g., retired from production use such as within the system of FIG. 1) as illustrated by 120.

What will now be described are various screenshots as may be included in a user interface in accordance with a system utilizing techniques described herein for qualification and maintenance as in connection with the lifecycle of such an instrument or computer system.

Figure 4:
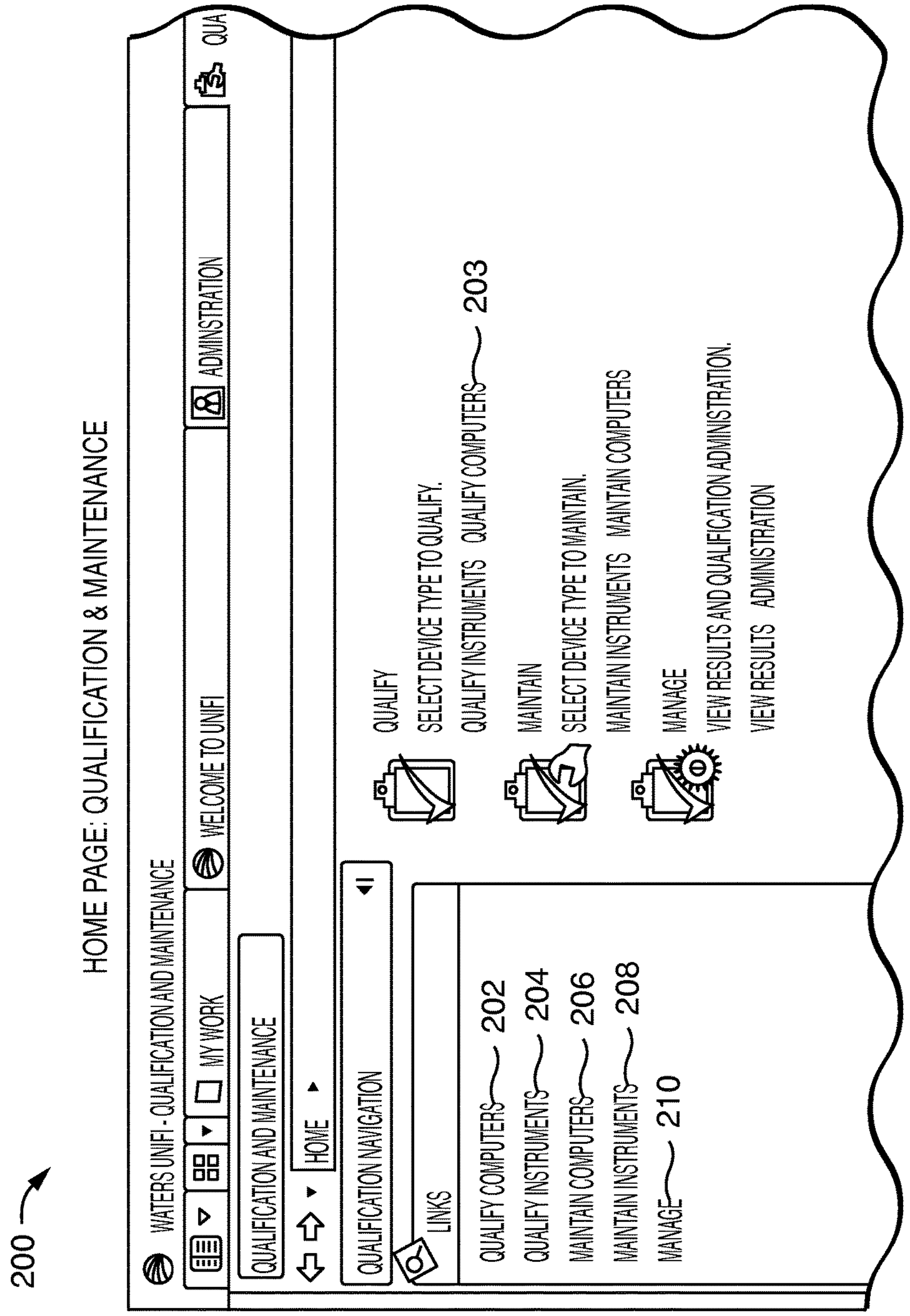
Figure 4A:
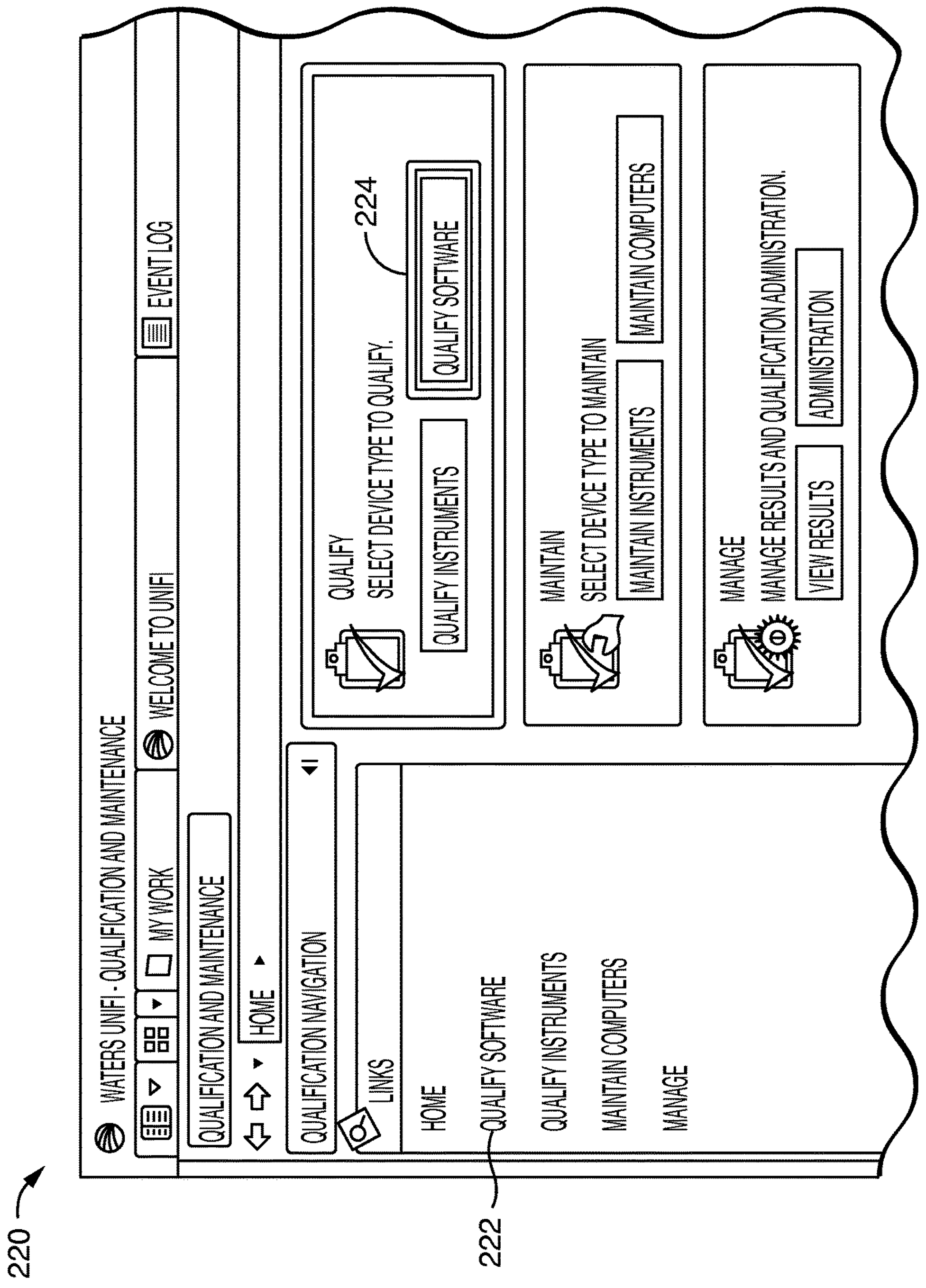

Referring to FIG. 4, shown is an example of a screenshot 200 that may be displayed in connection with a user interface home page for qualification and maintenance activities in an embodiment in accordance with techniques herein. The example 200 includes options related to instruments and computers. More generally, in the exemplary embodiment herein, instruments and computers may be referred to as devices included in a system utilizing techniques herein. The example 200 includes options for computer qualification 202, instrument qualification 204, computer maintenance 206, instrument maintenance 208 and management 210. In connection with computer qualification 202, such qualification may also be characterized as including the qualification of the software on one or more computer systems. In an embodiment implementing user interface (UI) screenshots in accordance with a variation of that illustrated in this and following figures, relevant UIs may display "Qualify Software" rather than "Qualify Computers". As an example, reference is made to FIG. 4A which shows an alternate exemplary UI display for a home page rather than as in FIG. 4. Similar modifications in connection with the displayed UI may be made in connection with other figures illustrated herein. In FIG. 4A, note the use of 222 and 224 rather than 202 and 203 of FIG. 4.

With reference back to FIG. 4, it should be noted that a display including the information and options of the example 200 may also include other additional options such as for performing verification processing to document or provide evidence of correct operational or performance aspects of the system such as may be related to qualification testing as well as correct performance of other aspects of functionality provided by the data system such as in connection with administrative activities, security and roles assigned to users to ensure particular user can/cannot perform certain operations in accordance with such assigned security limitation and roles. For example, verification may include setting instrument control parameters using software of the data system and then verifying those settings, verifying access, security and control settings of the data system (e.g., verifying that only particular users having appropriate privileges can perform certain operations), and the like.

Figure 5:
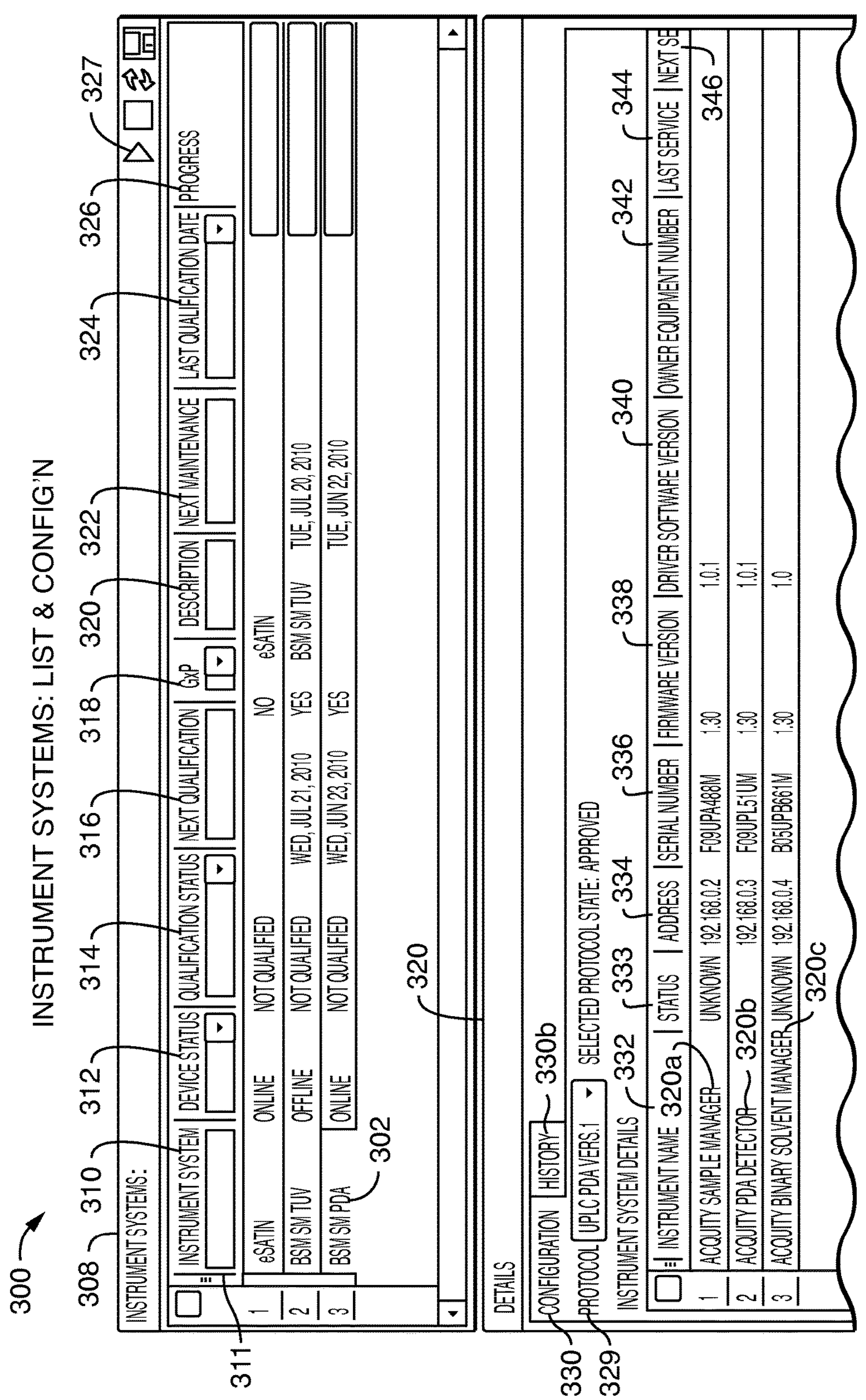

Selecting element 204 may result in display of a screenshot as illustrated in FIG. 5. It should be noted that the menu options and activities that may be performed in connection with FIG. 4 illustrates activities that may be performed in connection with a system which is characterized as regulated in accordance with government regulations, though non-regulated systems can also be qualified, verified, or validated as well in an embodiment in accordance with the techniques herein.

Referring to FIG. 5, shown is an example of a screenshot that may be displayed in response to selecting element 204 of FIG. 4 related to instrument qualification. The example 300 includes a top portion 308 that may list all the instruments or instrument systems such as may be included in an embodiment as illustrated in FIG. 1. Each row of the top portion 308 may include information on a particular instrument system such as for each LC, MS, and the like. Information included in a row of the top portion 308 for each displayed instrument system may include an instrument system identifier or name 310, device status 312 (e.g., whether the device in online or available for use or otherwise offline/not available for use), qualification status 314 (e.g., whether the instrument is currently qualified, unqualified, whether qualification is in-progress/pending), next qualification 316 (e.g., a date as to the next scheduled or required qualification. Note that this may be based on a schedule or may be updated in response to performing and/or logging a maintenance or repair activity), an indicator 318 as to whether the instrument is regulated or unregulated (e.g., whether the instrument is subject to regulations, requirements or standards such as governmental related regulations, requirements and/or standards), a description 320, next maintenance 322 (e.g., date as to the next scheduled maintenance), last qualification date 324 (e.g., last previous date as to last successful qualification), progress 326 (e.g., whether qualification processing is currently in progress and an indication as to how far along the qualification processing is). The qualification status 314 may indicate a current state regarding qualification of each listed instrument and may be one way by which a user may be notified as to the qualification status of the instrument. When the qualification status of 314 for an instrument is not qualified or unqualified, the status 314 provides an indication to the user that requalification is needed as may relate to the occurrence of an event as described elsewhere herein. An embodiment may have the qualification status be one of any number of defined possible states. In one embodiment, two qualification states may be defined—qualified and unqualified (e.g., not qualified). An embodiment may also include the foregoing two possible states and one or more other defined states as may be desired. For example, an embodiment may include the qualification states of qualified, unqualified and pending (indicating that qualification processing is currently underway but not yet completed). When displaying a status of pending for qualification, the status may further indicate if an error has occurred in qualification testing performed up to a current point in time.

In one embodiment having two qualification states (qualified or unqualified) for the qualification status 314 of the instrument, the state 314 may indicate qualified if qualification testing is up to date and has been successfully performed in accordance with any periodic requalification requirements or performing requalification as may be needed responsive to a repair or maintenance activity (e.g., where the requalification may be performed as a confirmatory action to such activity). Otherwise, the status 314 may be "not qualified" or rather unqualified (e.g. such as if any of IQ, OQ and/or PQ testing has not been successfully performed in connection with a latest set of qualification tests, if an activity such as a maintenance or repair activity was performed and subsequent requalification has not yet been attempted or has not been successfully completed, and the like).

It should be noted that the information displayed in portion 308 may be further filtered and/or sorted based on a particular value entered into any one or more of the input fields included in row 311.

A particular device, such as instrument system 302, may be selected. Instrument system 302 may be an LC system which includes the components of an injector, detector, and a pump. For the selected instrument 302, a bottom portion 320 of the display may include additional information. The element 320 may include a configuration tab 330 and a history tab **330*b*. When the configuration tab 330 is selected as active, the currently displayed information for the selected LC instrument 302 may include 3 rows 320*a*-320*c* of additional detailed information for the various components of the selected LC instrument 302. The 3 rows 320*a*-320*c* provide additional configuration information, respectively, for the LC components of injector, detector and pump. Each of the foregoing rows 320*a*-320*c* may include a name for the component 332, status 333, IP address 334, serial number 336, firmware version 338, driver software version 340, owner equipment number 342, date of last service 344, date of next service 346, and the like. The driver software version 340 and/or firmware version 338** may relate to currently installed versions used to control the instrument and facilitate instrument communications with a computer system and other devices of the system.

The example 300 may include an arrow 327 that may be selected to commence performing qualification processing for the selected instrument 302. Selection of 327 may result in display of other screenshots (not illustrated) such as a dialogue to select qualification tests, a qualification protocol workflow assistant, and the like, and then commence performing qualification processing based on the dialogue.

Element 329 may denote a particular qualification protocol and an associated status such as approved or unapproved. The protocol status of approved/unapproved may indicate a status of review with respect to the selected protocol such as by a customer or other user in connection with whether the procedure and tests of the protocol accurately reflect testing in compliance with requirements or regulations that may be required. In one embodiment, the particular qualification protocol selected in 329 may be the protocol used in connection with subsequent selection of arrow 327.

Figure 6:
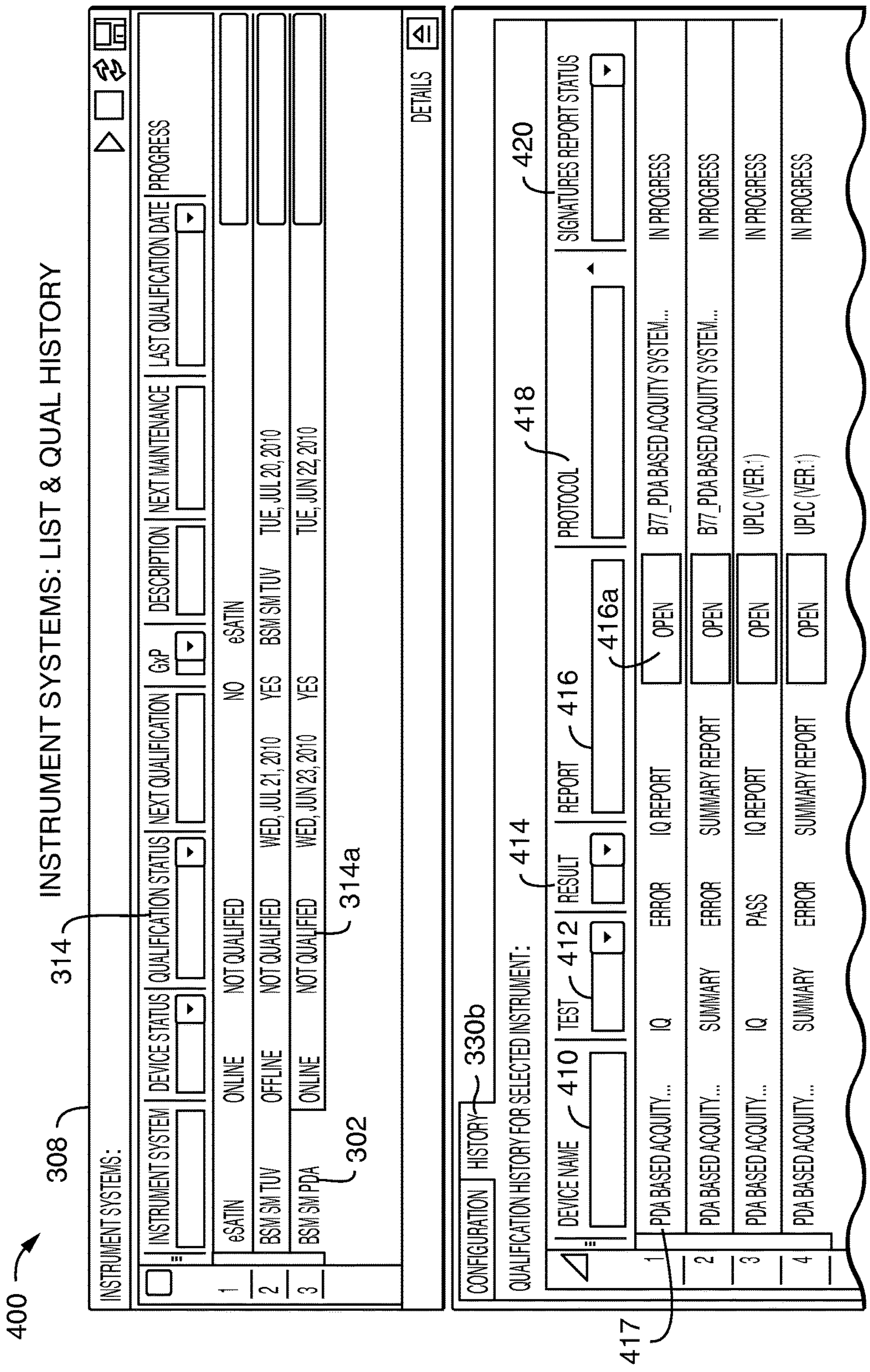

In response to selection of the history tab **330*b*, the bottom portion 320 of the display may be updated as illustrated in FIG. 6**.

Referring to FIG. 6, shown is an example 400 of the information that may be displayed in a screenshot in response to selecting the history tab **330*b* for the instrument system 302 of FIG. 5. In response, the qualification history for the selected instrument system 302 may be displayed. The qualification history displayed may include recorded information regarding qualification tests performed for the selected instrument system 302. Such information may include qualification test results as may be included in reports recorded automatically as a result of performing qualification testing. In this example, a row may be included in the qualification history information for each instance of a qualification result generated by executing a qualification protocol for the selected instrument. A qualification protocol may refer to a named procedure or process defining one or more tests for IQ, OQ and/or PQ for the particular instrument. In other words, a qualification protocol may be generally characterized as a defined process of tests performed related to any one or more of IQ, OQ and/or PQ. The particular test, parameters, and the like, may vary with the instrument, regulation or requirements for a regulated system, and the like. Each row in the qualification history may identify a device or instrument name 410 for the instrument within the system the history information applies to, identify the qualification test performed 412 (e.g., IQ only, summary for IQ, OQ and PQ), qualification result 414 (e.g., result of performing the protocol), report 416, protocol 418 (e.g., name of the testing protocol or procedure performed), signatures report status 420 (e.g., indication as to the progress and/or status as to whether necessary signatures have been obtained in connection with reviewing and/or approving the qualification protocol results and reports), and the like. Additionally, the user interface may provide an option to allow a user to select and review a qualification report. For example, a user may select element 416*a* to view the qualification report associated with the IQ testing represented by row 417**.

Thus, for an instrument system 302 having an unqualified/not qualified status 314 which is a regulated instrument system, a user may review summary information in 308 and may further drill down into the instrument's qualification history for further information regarding the current unqualified status of the instrument system and the individual modules within the instrument system. For example, in this case, the row of 302 indicates that there was no prior qualification so the instrument 302 may be newly commissioned and is being qualified for the first or initial time. The status 314*a* for the instrument system 302 is unqualified in that the IQ has passed but is not yet approved (420) and, additionally, errors occurred when performing the qualification tests for three of the four displayed qualification protocols (e.g., errors as identified in 414 for rows 1, 2 and 4).

Furthermore, as described in more detail below and elsewhere herein, the qualification status 314*a* may be set to unqualified, for example, as a result of performing a maintenance activity, or in response to a scheduled requalification.

Figure 7:
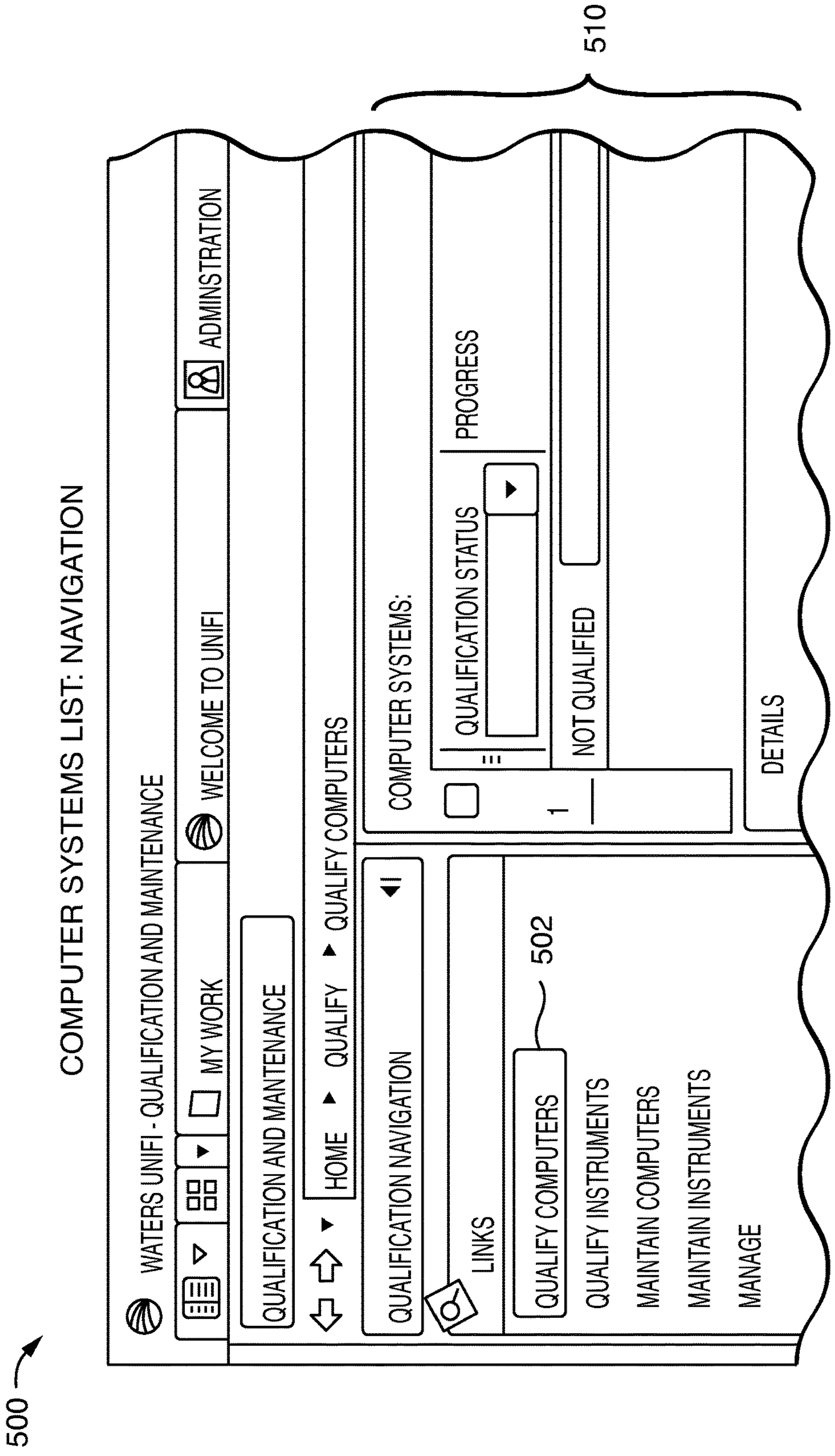

Referring to FIG. 7, shown is an example of the display of FIG. 4 in response to selecting qualify computers 502. The portion 510 may be updated to include information on devices which are computers rather than instruments.

Figure 8:
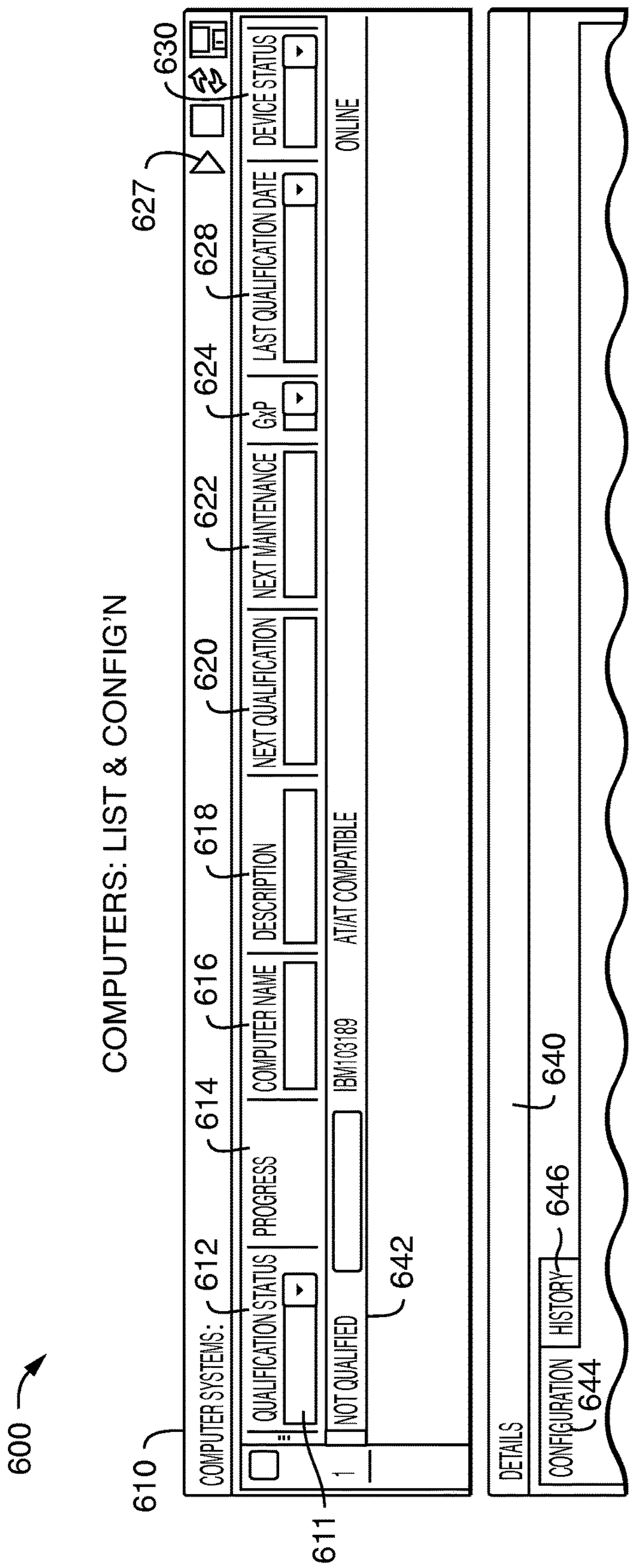

Referring to FIG. 8, shown in further detail is information of portion 510 in response to selecting 502 of FIG. 7. In a manner similar to that as described above for instruments in response to selecting 204 of FIG. 4, a top portion 610 of the display includes a list of the computers included in the system. A row of information may be included in 610 for each computer system. In this example, there is a single computer system as indicated by the single row of information in 610. Each row may include a qualification status 612, a progress indicating 614, a computer name 616, description for the computer system 618, date of next qualification 620, date of next maintenance 622, an indicator 624 as to whether the computer system is regulated or not, a date 628 of the last previous qualification, device status 630 (e.g., whether the device is online/available for use or offline/not available for use), and the like. In response to selecting a computer system as identified by a single row 642 from 610, the bottom portion 640 may be populated with further configuration or history details for the selected computer system. In this example, the computer system represented by 642 is currently not qualified. As will be described in more detail below, this current status of the computer system may be the result of performing and logging a maintenance activity.

It should be noted that the information displayed in portion 610 may be further filtered and/or sorted based on a particular value entered into any one or more of the input fields included in row 611.

The example 600 may include an arrow 627 that may be selected to commence performing qualification processing for the selected computer system 642. Selection of 627 may result in display of other screenshots (not illustrated) such as a dialogue to select qualification tests, a qualification protocol workflow assistant, and the like, and then commence performing qualification processing based on the dialogue.

Figure 9:
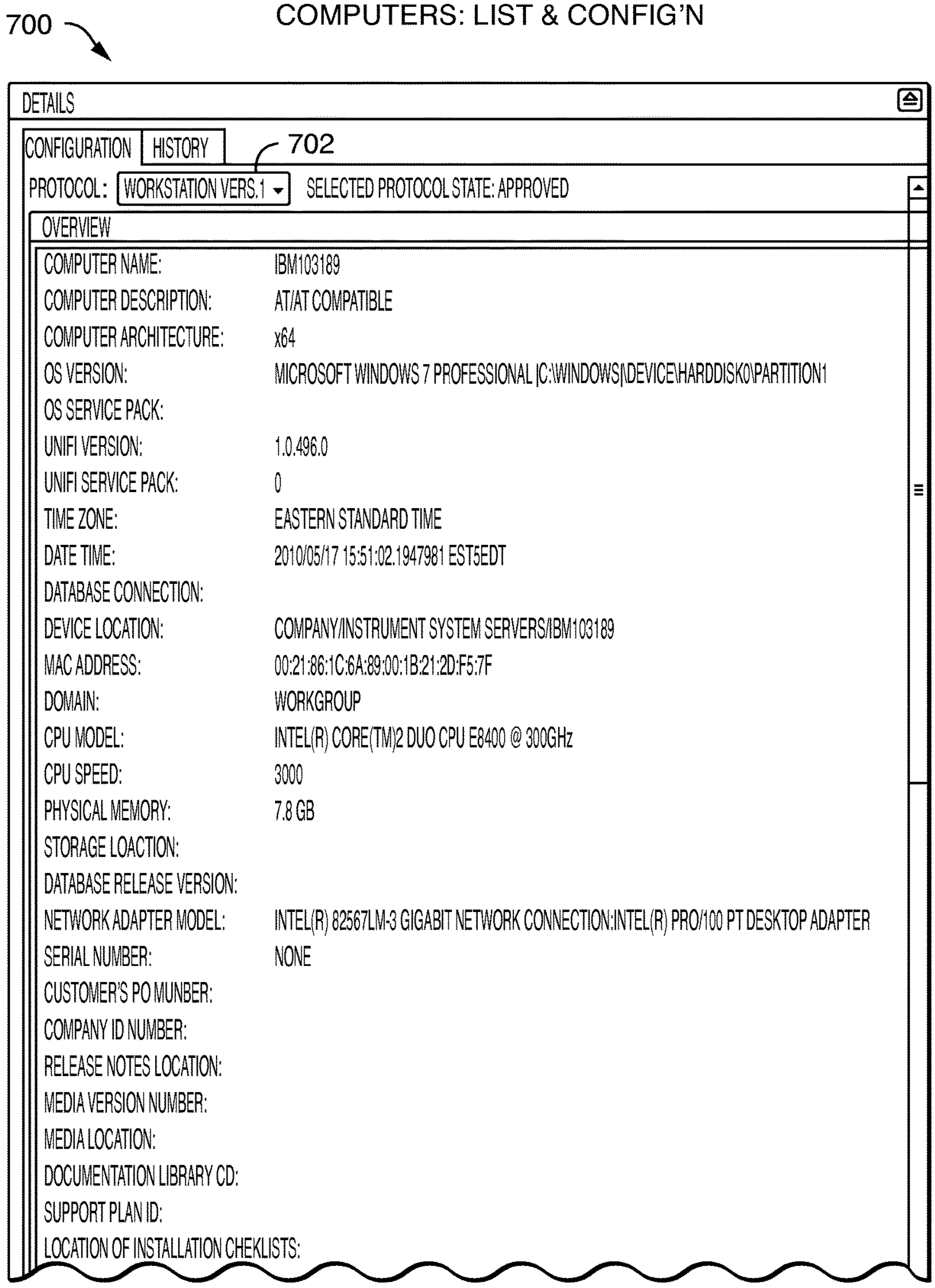

In response to selection of the configuration tab 644, the bottom portion 640 may be populated with configuration details as illustrated in FIGS. 9 and 10. FIG. 9 illustrates that the configuration information may include the computer name, description, architecture information, operating system information (e.g. operating system version and service pack installed), UNIFI version and service pack (e.g., information regarding the particular data system related software installed on the computer system), date/time information (e.g., time zone, date/time), database connections (if any), device location, MAC address, domain, CPU model, CPU speed, an amount of physical memory, database release version, network adapter model, serial number, customer information (e.g., purchase order (PO) number, company identifier), and other information (e.g., release notes location, media version number and location, documentation library CD, support plan identifier, location of installation checklists). FIG. 10 illustrates that the configuration information for the selected computer system may also include a listing of currently installed updates.

Referring back to FIG. 9, in a manner similar to element 329 of FIG. 5, element 702 may denote a particular qualification protocol and an associated status such as approved or unapproved. The protocol status of approved/unapproved may indicate a status of review with respect to the selected protocol such as by a customer or other user in connection with whether the procedure and tests of the protocol accurately reflect testing in compliance with requirements or regulations that may be required. In one embodiment, the particular qualification protocol selected in 702 may be the protocol used in connection with subsequent selection of arrow 627 of FIG. 8.

Although not further illustrated, selection of the history tab 646 of FIG. 8 provides for a display of the qualification history for the computer system in a manner similar to that as described above for an instrument. However, as also discussed elsewhere herein, the particular qualification tests for IQ, OQ and/or PQ are for the computer system and related activities thereof rather than a scientific instrument or other device. For example, a new operating system service pack, device driver, operating system update, memory upgrade, and the like, may be installed on the computer system as part of a maintenance activity for a computer system. In connection with an instrument that performs LC, maintenance activities may include, for example, changing a seal, needle or syringe.

Figure 11:
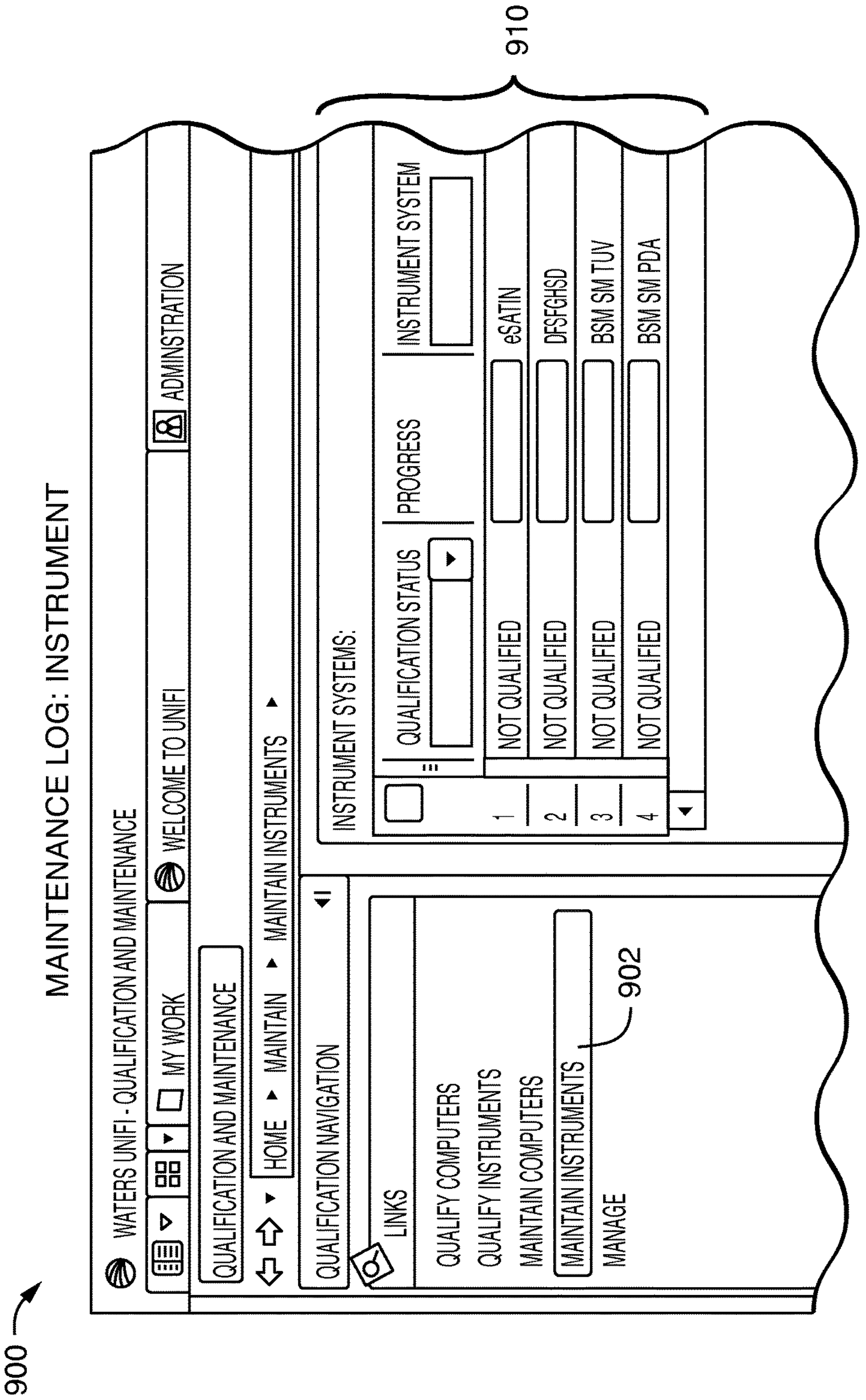
Figure 12:
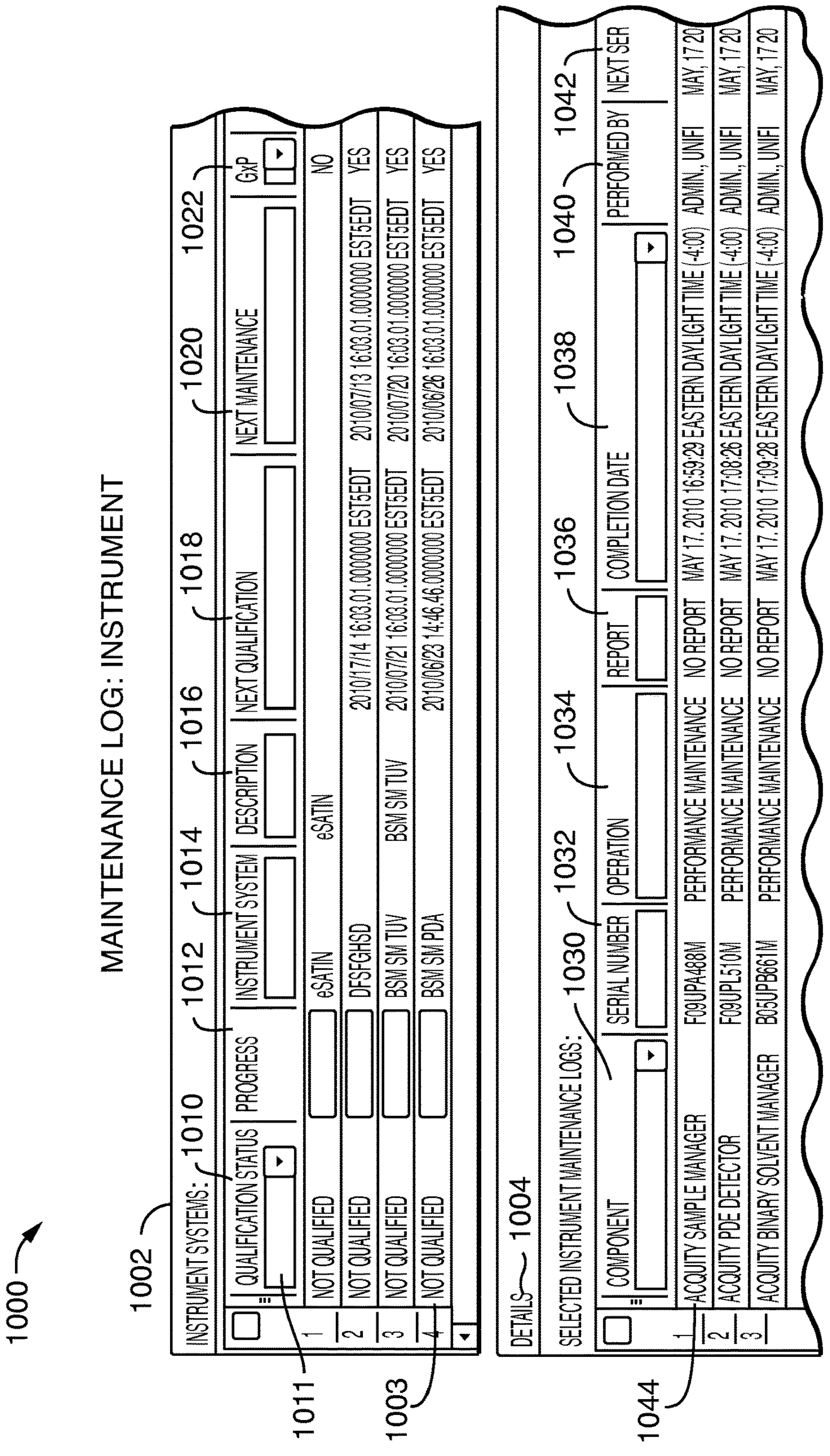

Referring to FIG. 11, shown is an example of a screenshot as may be displayed in a user interface in connection with selecting an option for maintenance of instruments 902 from a main navigation panel similar to that as displayed in connection with FIG. 4. In response to selecting 902, portion 910 of the display may be updated to provide information on instrument maintenance. FIG. 12 provides additional detail regarding information that may be included in portion 910 of FIG. 11. It should be noted that the menu options categorized as maintenance may also include activities related to repairs. In other words, the logs, history, and the like, associated with the maintenance menu options may include activities referred to as maintenance (e.g., such as may be performed in an ongoing basis when the instrument is operable and available for production use) and repair (e.g., such as may occur when an instrument becomes inoperable requiring repairs).

The example 1000 of FIG. 12 may include a top portion 1002 which displays summary information regarding maintenance activities for the listed instrument systems. A row is included in 1002 for each instrument system and may include qualification status 1010, a progress indicator regarding qualification, information 1014 identifying the instrument system, a description 1016 for the instrument system, a date of next qualification 1018, a date of next maintenance, a regulation indicator 1022 as to whether the instrument system is regulated (e.g., subject to compliance with regulations, standards and/or requirements). The information for each instrument included in a row of 1002 is similar to as described elsewhere herein in connection with other displays. It should be noted that the information displayed in portion 1002 may be further filtered and/or sorted based on a particular value entered into any one or more of the input fields included in row 1011. An instrument system may be selected from portion 1002 by selecting a particular row, such as 1003. In response, the bottom portion 1004 is updated to reflect maintenance details for the selected instrument system 1003. In this example, instrument 1003 is an LC system as described above and may include components of a pump, detector and injector as noted elsewhere herein. Portion 1004 is updated to display maintenance information for each such component of the selected LC system, where each row in 1004 may display maintenance information for one component of the selected LC system. Each row in 1004 may identify a component 1030, serial number 1032 of the component, operation 1034, report indicator 1036, maintenance completion date 1038, user identifier who performed the maintenance 1040, date of next scheduled maintenance activity 1042, and the like. A record or row of 1004 may be included for each logged maintenance activity. In this example, no report has been created for any of the listed maintenance activities.

Figure 12A:
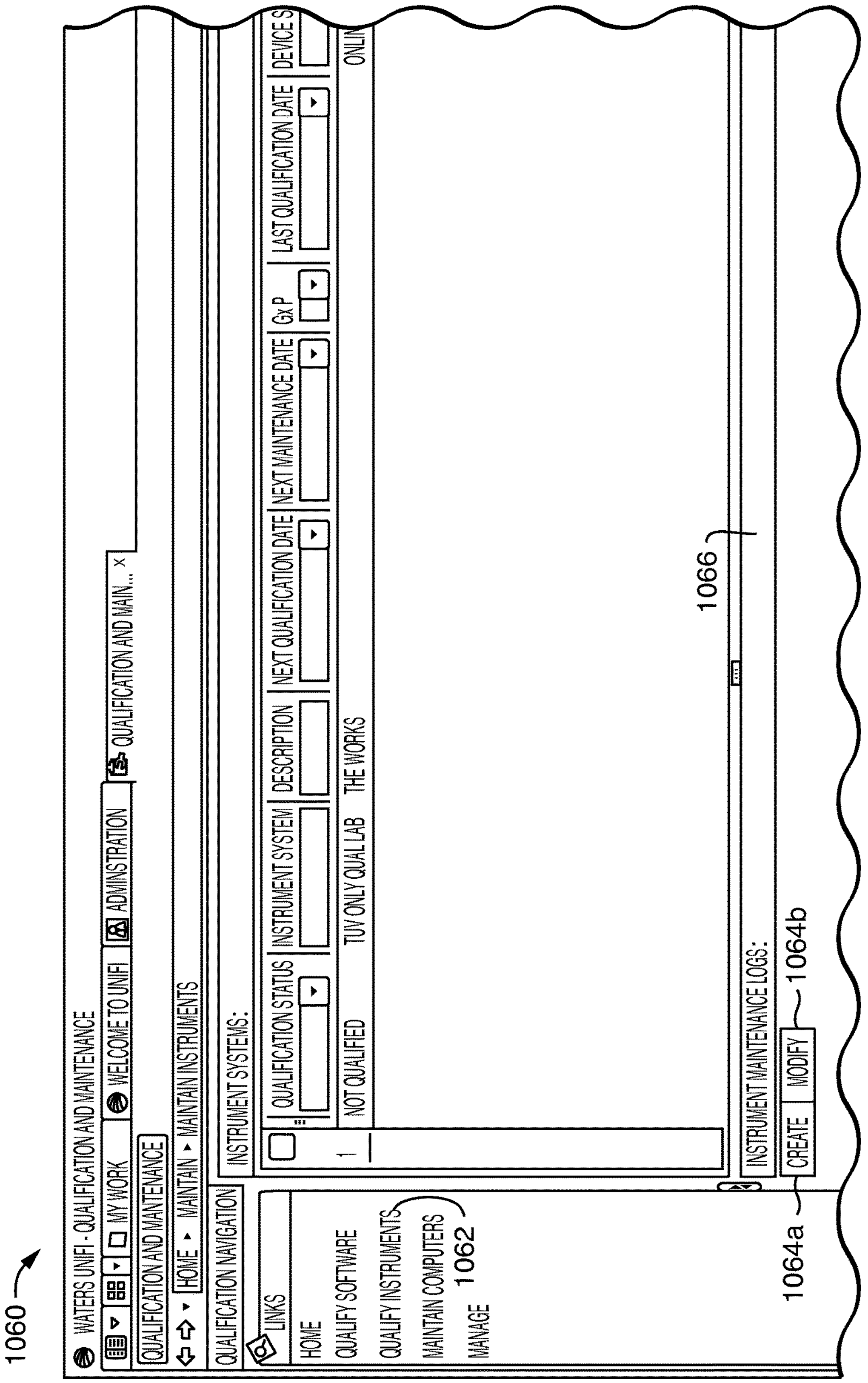

In order to create a report and enter additional information for a maintenance activity, reference is now made to FIG. 12A illustrating an example screenshot that may be displayed in connection with creating a new maintenance activity log or modifying an existing such activity log. The example 1060 includes a bottom portion 1066 which may be displayed in connection with performing a selection to create a new maintenance activity log or modifying an existing log. The portion 1066 includes two tabs—Create and Modify. When the create tab 1064*a* is selected, a dialogue to create a new maintenance log may commence. When the modify tab 1064*b* is selected, the user may be presented with a list of existing maintenance logs (not illustrated) from which the user may make a selection of a particular listed log. In response to such a selection, a dialogue to modify the existing selected log in which the existing information of the log may be displayed for editing. The displays in connection with the foregoing creation dialogue and modification dialogues may be similar with the difference that the modification dialogue may populate the display with existing information from the previously created and selected maintenance log.

In response to selecting 1064, the user may be presented with one or more screenshots to obtain information in connection with creating a new maintenance activity log. For example, in response to selecting 1064, the display of FIGS. 13 and 14 may be presented to the user to input information regarding the maintenance activity. As illustrated in FIG. 13, the user may enter information identifying the instrument component or module 1102, serial number 1104 of the instrument component, one of a series of predefined maintenance operations 1106, service completion date 1107, user identifier 1108 performing the maintenance activity, date when next service is due 1110 (e.g., may be automatically calculated and populated based on requirements or regulations), approvals 1112 of the logged maintenance activity, and any comments 1114. It should be noted that fields denoted by "*" may indicate required input fields in connection with this and other displays.

In one embodiment in response to selecting 1064 of FIG. 12A, the user may be presented with the display of FIG. 14 to obtain information in connection with the maintenance activity. The example 1200 includes four screen portions 1210, 1220, 1230 and 1240. Element 1210 may represent the completed entry of information as illustrated in FIG. 13. Element 1220 may include information regarding the maintenance or repair details including a reason 1220 for the repair, a repair description 1224, a repair type 1226, a repair status 1228 and a repair severity 1229. In this example 1220 for the LC component, preventive maintenance is performed to replace the needle and seals and recalibrate the seal pack. This maintenance activity may be classified based on repair type 1226, status 1228 and severity 1229.

In one embodiment in accordance with techniques herein, the repair severity indicated by 1229 may be one of a plurality of defined severity levels as may be defined in a system policy. The policy may define which one or more severity levels requiring requalification or other confirmatory actions. For example, one embodiment may define three levels of severity, from lowest to highest as—low, moderate and high. The policy may indicate which one or more repair severities when entered in 1229 cause the qualification status of the instrument to be unqualified or not qualified. The foregoing qualification status may be reflected in one or more different user interface indicators such as described elsewhere herein (e.g., element 314 of FIG. 6, element 612 of FIG. 8). More generally, repair severity may be included in requalification criteria indicating whether requalification is required. Also, more generally, the policy may define other responses and aspects of a system that may be modified due to the qualification criteria. For example, a maintenance activity may be performed having a high severity and the policy may indicate that high severity repairs require requalification. Furthermore, the policy may also indicate that until the completion of required confirmatory actions (such as successful requalification) in response to performing the foregoing high severity maintenance activity, the instrument and/or one or more components comprising the instrument may be blocked from regulated/production use for instance which may be by being disabled and set offline for further production use. The status of disabled or offline may be reflected in one or more user interface indicators such as, for example, device status 312 of FIG. 5 and component status 333 of FIG. 5. The requalification criterion/criteria is described herein as including at least repair severity and may also include other criteria such as, for example, whether the device (e.g., instrument or computer system) is regulated, based on repair type 1226, aspects related to risk based for instance on novelty, complexity, and use of the device (e.g., category, technology, number of components in the instrument, particular software installed on a computer system, patient safety/product quality/data integrity risk), and the like.

Element 1230 represents a portion of the display relating to supporting documentation such as the electronic training certification of the individual performing the maintenance or repair activity, or calibration certificates for instruments used in qualification service activities. Element 1240 may represent a portion of the display relating to tracking and trending information related to the maintenance or repair activity. The information of 1240 may include, for example, the repair provider, labor expense, parts expense, whether this is a first time or a follow on repair (e.g., related to a previously performed repair or maintenance activity), a cost center, the total downtime due to the maintenance or repair, and amount of time taken to perform the repair. Information of 1240 may be analyzed and examined over time, such as in automated fashion using software and/or through manual examination, to determine trends and track maintenance and repair information over time. For example, for a particular instrument, computer system or other device, information of

1240 may be used to determine and aggregate amount of repair and/or maintenance time, total downtime due to maintenance and repairs performed during a defined time period or over the life of a device to date, total expenses such as for labor and/or parts over a time period, and the like. A system may define triggers based on detection of particular trends. For example, if costs or total downtime exceed a certain threshold, a notification may be sent or flag applied to the system and the system or a particular component of the system may be decommissioned and replaced with a new system or component.

Figure 15:
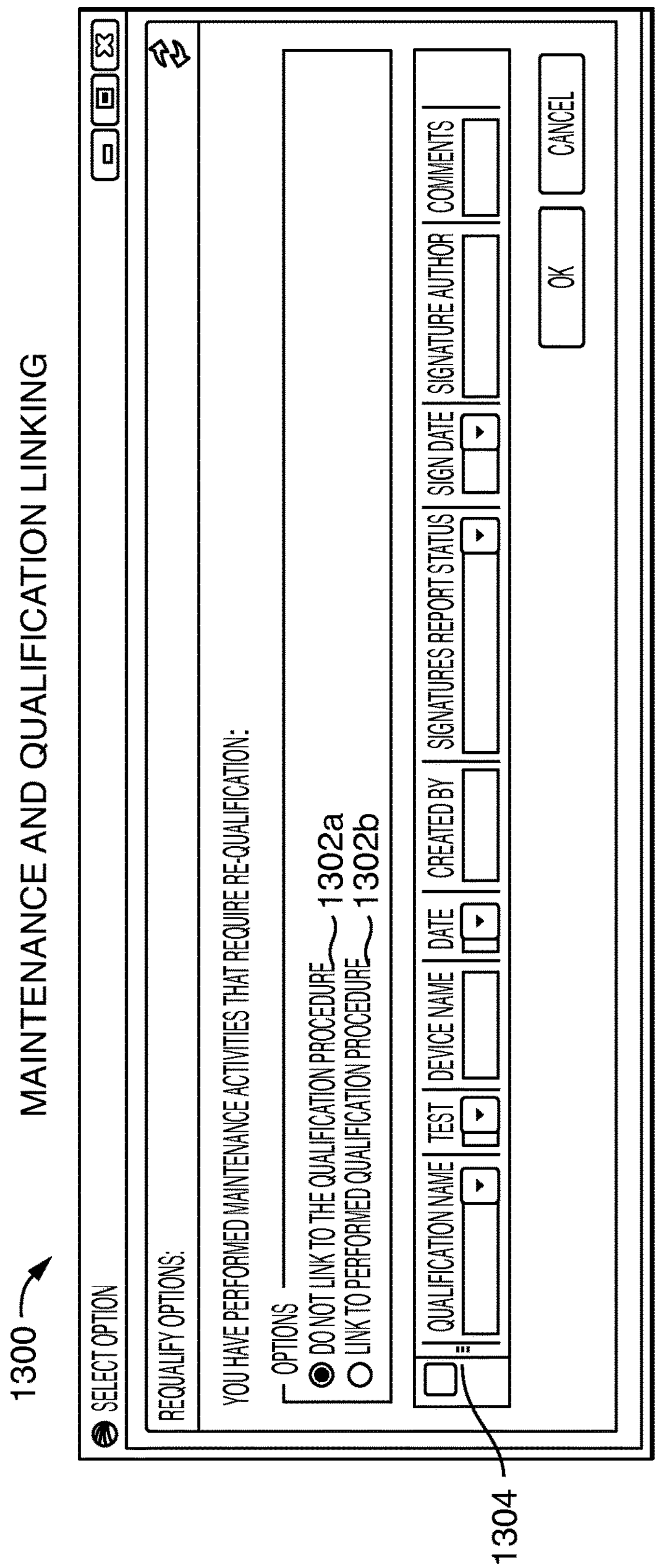

Referring to FIG. 15, shown is an example of a screenshot that may be displayed in response to automatically determining in accordance with requalification criteria that a maintenance activity requires requalification. In response, the user may be presented with the display of example 1300 notifying the user that the maintenance activity being logged requires requalification and inquiring whether to link to a performed qualification procedure. In the example 1300, a selection has been made 1302*a* to not link the maintenance activity to a performed qualification procedure and the device's qualification status may be accordingly updated to reflect not qualified or unqualified. In one embodiment, the user may be allowed to enter the maintenance activity information after actually performing both the maintenance activity and the requalification. In this case, the user may link or associate the maintenance activity information with the particular requalification as may be captured in an existing requalification report by selecting option 1302*b* and entering the information of 1304 to identify the requalification instance.

As a variation to the foregoing, a user may be prompted with a display in response to automatically determining in accordance with requalification criteria that a maintenance activity requires requalification. As above, the display may notify the user that the maintenance activity being logged requires requalification. The user may then be prompted with an inquiry as to whether to commence performing requalification such as by launching execution of a qualification dialogue. The results of the qualification processing may be linked to the maintenance or repair activity An embodiment may also provide other ways in which a subsequent requalification may be linked to a maintenance or repair activity. For example, a user may perform the maintenance activity and then at a later date perform the requalification testing. In this case, when performing the requalification testing, the user may be presented with options to link the requalification to a logged maintenance activity. For example, as part of the qualification testing dialogue, the user may enter information to link the qualification testing for an instrument to one or more maintenance activities of the instrument so that the system may automatically update any status information such as regarding the instrument, its components, and the like.

Figure 16:
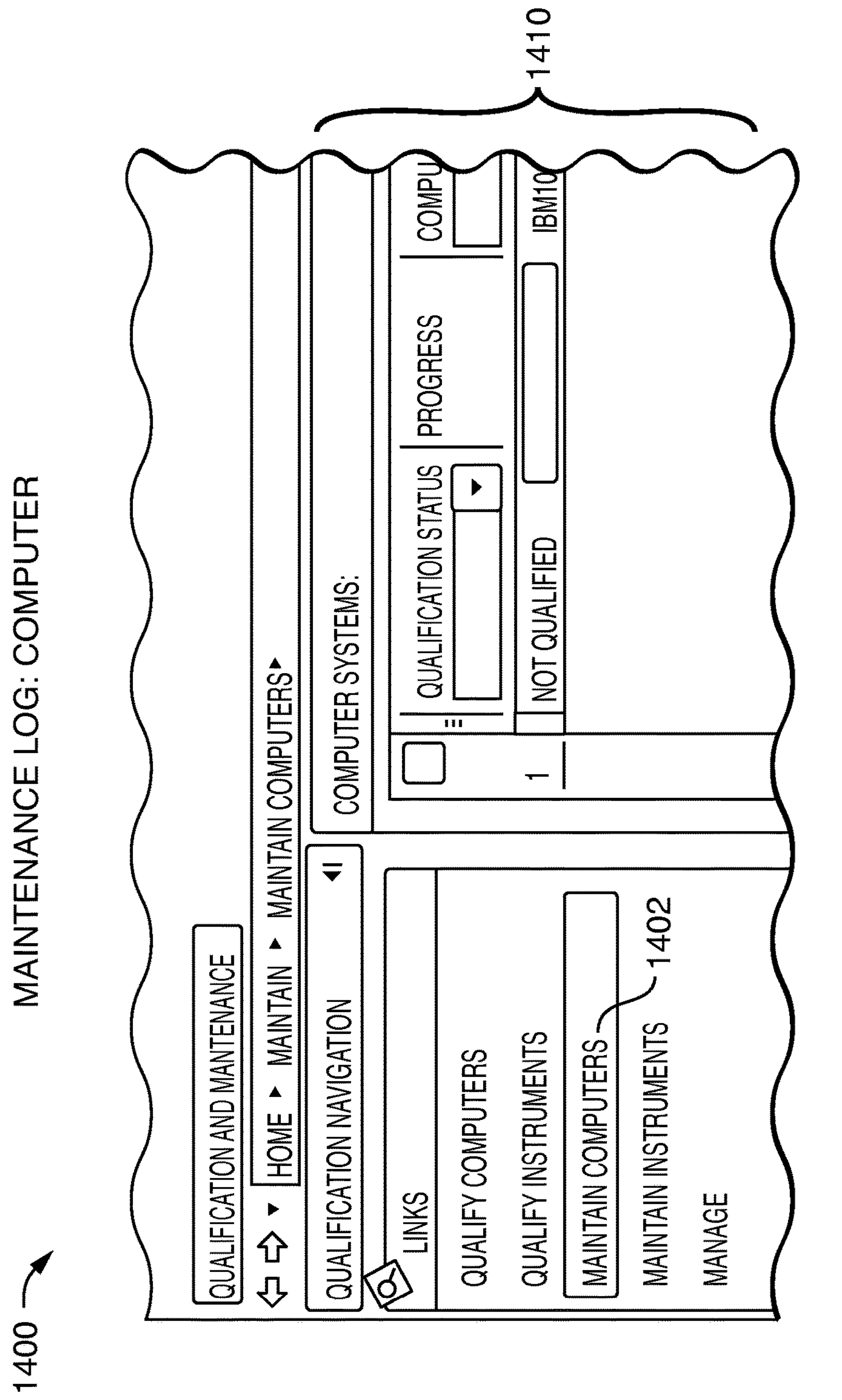
Figure 17:
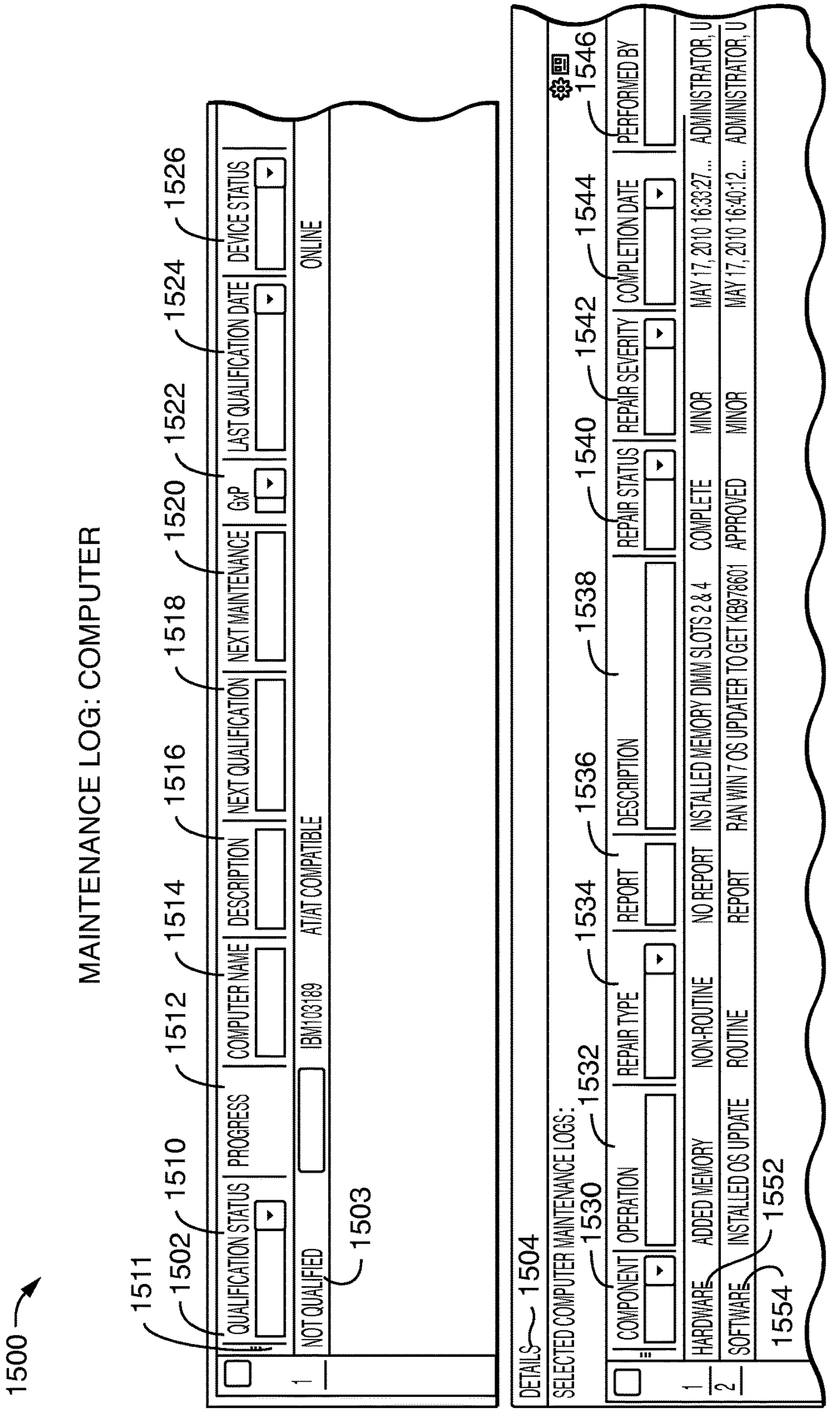

Referring to FIG. 16, shown is an example of a screenshot as may be displayed in a user interface in connection with selecting an option for maintenance of computers 1402 from a main navigation panel similar to that as displayed in connection with FIG. 4. In response to selecting 1402, portion 1410 of the display may be updated to provide information on instrument maintenance. FIG. 17 provides additional detail regarding information that may be included in portion 1410 of FIG. 16.

The example 1500 of FIG. 17 may include a top portion 1502 which displays summary information regarding maintenance activities for the listed computer systems in a manner similar to that as described above for instruments. A row is included in 1502 for each computer system and may include qualification status 1510, a progress indicator 1512 regarding qualification, information 1514 identifying a name for the computer system, a description 1516, a date of next qualification 1518, a date of next maintenance 1520, a regulation indicator 1522 as to whether the instrument is regulated (e.g., subject to compliance with regulations, standards and/or requirements), a date of last qualification 1524 and device status 1526. It should be noted that the information displayed in portion 1502 may be further filtered and/or sorted based on a particular value entered into any one or more of the input fields included in row 1511.

A computer system may be selected from portion 1502 by selecting a particular row, such as 1503. In response, the bottom portion 1504 is updated to reflect maintenance details for the selected computer system 1503. In this example, there is a single computer system illustrated by a single row in 1502. Portion 1504 is updated to display maintenance information for each such component (e.g. various hardware and/or software components) of the selected computer system, where each row in 1504 may display maintenance information for one component of the selected computer system. Each row in 1504 may identify a component 1530, an operation performed 1532, a repair type 1534, a report indicator 1536, a description 1538, a repair status 1540, a repair severity 1542, a maintenance completion date 1544, a user identifier of who performed the maintenance 1546, and the like. A record or row of 1504 may be included for each logged maintenance activity. In this example, there are two logged maintenance activities 1552 and 1554. What will now be described are screenshots that may be presented to the user in connection with obtaining additional information for each of the foregoing 1552 and 1554.

Referring to FIG. 18, shown is an example of a screenshot that may be used in connection with entering maintenance activity information regarding element 1552 for the hardware component. The example 1600 illustrates information that may be provided in connection with adding memory to the computer system as part of a planned upgrade. The example 1600 includes four screen portions 1610, 1620, 1630 and 1640 containing information similar to that as described in connection with FIG. 14. Processing as described above in connection with a maintenance activity for an instrument may also be performed in connection with maintenance activities for a computer system such as illustrated in FIGS. 18 and 19. In a manner similar to that as described above with FIG. 14, the repair severity 1622 may be one of a plurality of defined severity levels as may be defined in a system policy. The policy may define which one or more severity levels requiring requalification or other confirmatory actions. For example, one embodiment may define three levels of severity, from lowest to highest as—low or minor, moderate and high. The policy may indicate which one or more repair severities when entered in 1622 cause the qualification status of the instrument to be unqualified or not qualified. The foregoing qualification status may be reflected in one or more different user interface indicators such as described elsewhere herein. More generally, as also described above, the repair severity may be included in requalification criteria indicating whether requalification is required and the policy may define other responses and aspects of a system that may be modified due to the qualification criteria. In the event that the maintenance activity logged with 1600 indicates a requalification is needed, testing may be performed as described above, for example, in connection with FIG. 15.

Referring to FIG. 19, shown is an example of a screenshot that may be used in connection with entering maintenance activity information regarding element 1552 of FIG. 17 for a software component. The example 1700 illustrates information that may be provided in connection with installing an operating system update. The example 1700 includes four screen portions 1710, 1720, 1730 and 1740 containing information similar to that as described in connection with FIG. 14. In a manner similar to that as described above with FIGS. 14 and 18, the repair severity 1722 may be one of a plurality of defined severity levels as may be defined in a system policy. The policy may define which one or more severity levels requiring requalification or other confirmatory actions. For example, one embodiment may define three levels of severity, from lowest to highest as—low or minor, moderate and high. The policy may indicate which one or more repair severities when entered in 1722 cause the qualification status of the instrument to be unqualified or not qualified. The foregoing qualification status may be reflected in one or more different user interface indicators such as described elsewhere herein. More generally, as also described above, the repair severity may be included in requalification criteria indicating whether requalification is required and the policy may define other responses and aspects of a system that may be modified due to the qualification criteria. In the event that the maintenance activity logged with 1700 indicates a requalification is needed, qualification testing may be performed as described above, for example, in connection with FIG. 15.

In connection with the foregoing such as with reference to FIG. 3, an embodiment in accordance with techniques herein may define one or more types of trigger events. An occurrence of a trigger event causes a notification to be provided regarding a responsive action or activity to be performed. Such trigger events may be caused by an occurrence of a time-based event, a trend-based event, a performance-based event, a usage based event and/or an unscheduled or other type of event. A time-based event may be, for example, a required maintenance or other activity such as may be scheduled based on a date/time basis (e.g., calendar-based scheduled event). A usage-based event may be based on a number of usages of an instrument (e.g., number of injections for an LC), component of an instrument (e.g., pump, injector, detector of an LC), part of a component (e.g., such as a needle, seal, etc of an LC), and the like. A performance-based event may be based on performance of an instrument, computer system, or other device. Performance-based criteria may be defined which varies by device (including type of instrument). For example, for a computer system, performance based criteria may be measured in terms of user response time to perform a particular requested operation. For an instrument performing MS, the performance criteria may be defined in terms of the instrument's mass accuracy performance. For an instrument performing LC, the performance criteria may relate to peak tailing. An LC may have an unacceptable amount of peak tailing. As known in the art, a chromatographic peak may be labeled as tailing or asymmetrical when it deviates from the ideal, symmetrical shape of a Gaussian peak. As one example of a tailing peak, a later eluted half of the peak may be wider than the front half of the peak. An unacceptable amount of peak tailing may adversely affect other processing such as, for example, peak detection (e.g., the end of the peak may be shown to be in different places for multiple injections of the same tailing peak and may cause an error in the peak area measurement.) To detect whether specified performance criteria is met, testing such as related to PQ, calibration or other testing may be performed. An unscheduled event may relate to a repair required for a device such as an instrument or computer system, or component thereof, that becomes inoperable or malfunctions. An unscheduled event may be related to a detected trend over time such as in connection with system suitability results or control samples, an amount of downtime, risk brought about due to a high number of cumulative changes made to a system or component thereof within a certain time period, performing more than a threshold number of unscheduled repairs needed due to components or parts, and the like. As such, a trend-based event occurrence may also be a particular type of unscheduled event. An unscheduled event may be, for example, receiving notification about a need to perform an unexpected hardware and/or software update or upgrade for a computer system or instrument. Upon the occurrence of a trigger event with respect to a device (such as an instrument or computer system), a user may be provided with notification to perform an action or activity responsive to the event occurrence. The action may include any of performing a maintenance activity, repair activity, and/or a test for the device. The test may be a qualification test, calibration test, and the like. Qualification tests are described above and may be related to IQ, OQ and/or PQ. Calibration may relate to, for example, calibrating an instrument to ensure preciseness in measurements with respect to a known calibration curve or standard. For example, consider an instrument that may require requalification based on occurrence of a usage-based or time-based event. For an LC system with a usage-based trigger defined, requalification may be performed after performing a specified number of injections. In this case, the responsive action may be to perform requalification testing with or without any required maintenance or repair activity. As another example, consider a usage-based trigger for a part of an instrument such as a seal or needle of an LC system. After performing a defined number of uses with a seal or needle, compliance with company standard operating procedures or the manufacturer's recommended maintenance guidelines may specify that the needle or seal be replaced. As such, upon the occurrence of a defined usage-based event, the required action may include performing a maintenance activity for such replacement. Further, the company standard operating procedure or manufacturer's guidelines may also require performing one or more further confirmatory actions in response to performing the maintenance activity. Such confirmatory actions may include performing one or more tests such as for requalification, calibration, and the like. Performing a test, either as an action directly from an event-based trigger occurrence or as a confirmatory action, may cause information to automatically be logged in the system regarding the test performed, results, and the like. As described above, maintenance or repair activities may require a user to log the particular activity/ies performed in a maintenance log record. In response to information entered in connection with the maintenance log record, further confirmatory actions may be required such as performing one or more tests related to qualification, calibration and the like. A severity may be associated with a maintenance activity and may dictate the level of confirmatory testing required, if any, to return the system to production use. The performance of certain activities which may pose a compliance issue for regulated system may be flagged and noted in the system, such as through the UI indicators, to notify the user. Depending on the severity, whether the device is regulated or not, and possibly other criteria associated with an activity performed to a system and/or the complexity of the system, the system may be disqualified and/or disabled from further use until any required confirmatory actions are performed. An embodiment may also modify one or more status aspects of the system upon the occurrence of a trigger. For example, upon the occurrence of a usage-based trigger or time-based trigger requiring requalification to be performed, the system may have an associated status of disqualified and/or be disabled from further use until the required qualifications and any other confirmatory actions are successfully performed.

As described above, policies may be defined providing for assigning a qualification status for a device (such as an instrument or computer system) based on criteria including one or more factors such as may be related to an event occurrence and/or activity performed in response to an event occurrence. For example, based on the severity level associated with performing a maintenance or repair activity, where the severity level may be any of minor, moderate or major associated with a maintenance activity, performing such an activity may result in changing the qualification status of one or more components of an affected instrument or computer system to unqualified. Other factors that may affect the qualification status and may be included in the criteria include the complexity of the affected instrument or computer system, type of repair, and the like. The criteria and resulting device and/or component qualification status may be predefined or preassigned such as by an administrator. Other embodiments may also allow such resulting qualification status assignment to be ad hoc by a user. In other words, the user performing the activity and logging the activity may be allowed to assign the resulting qualification status for one or more components as a result of the logged activity. An embodiment in accordance with techniques herein may automatically create or interact with the user to create the maintenance log as a result of, or responsive to, the system or device detecting that the user performs such activities. Alternatively, an embodiment may allow a user to perform the activity and then have the user log the activity without such automation in detecting the activity. As a variation to the foregoing, an embodiment may also assign a resulting qualification status and/or state of a device, and/or state of a component thereof based on an occurrence of a defined trigger. For example, failure to perform time-based or usage-based qualification within a certain amount of time or by the required due date may result in the automatic disqualification status and may also result in automatically disabling further use of the instrument and/or component that is disqualified until such required qualification is successfully performed.

As mentioned above such as in connection with FIG. 4, an embodiment in accordance with techniques herein may include other functionality related to other types of testing besides qualification testing. For example, an embodiment may perform verification testing which is described elsewhere herein. In this case, an embodiment may also include functionality therein to link or logically associate such testing information with other records, such as with maintenance or repair logs. This may be performed in a manner similar to that as described herein with qualification testing activities. Additionally, in a manner similar to qualification testing, performing verification testing may also be an action performed in response to an occurrence of a trigger event and may also be included in confirmatory action(s) performed in response to a maintenance or repair activity.

Qualification testing performed such as in connection with a qualification protocol as an action (confirmatory or otherwise) may include performing any of IQ, OQ and/or PQ as may vary, for example, with device and/or regulatory requirements. To further illustrate with respect to a device that is an LC system including a pump, injector and detector, the qualification processing performed may include performing IQ, OQ and PQ tests. IQ may include, for example, ensuring that electrical connections for the installed components are operable and other factors regarding the installation environment. OQ and/or PQ tests may include, for example, tests for accuracy of temperature and flow rate such as to within an acceptable threshold level of accuracy.

Figure 20:
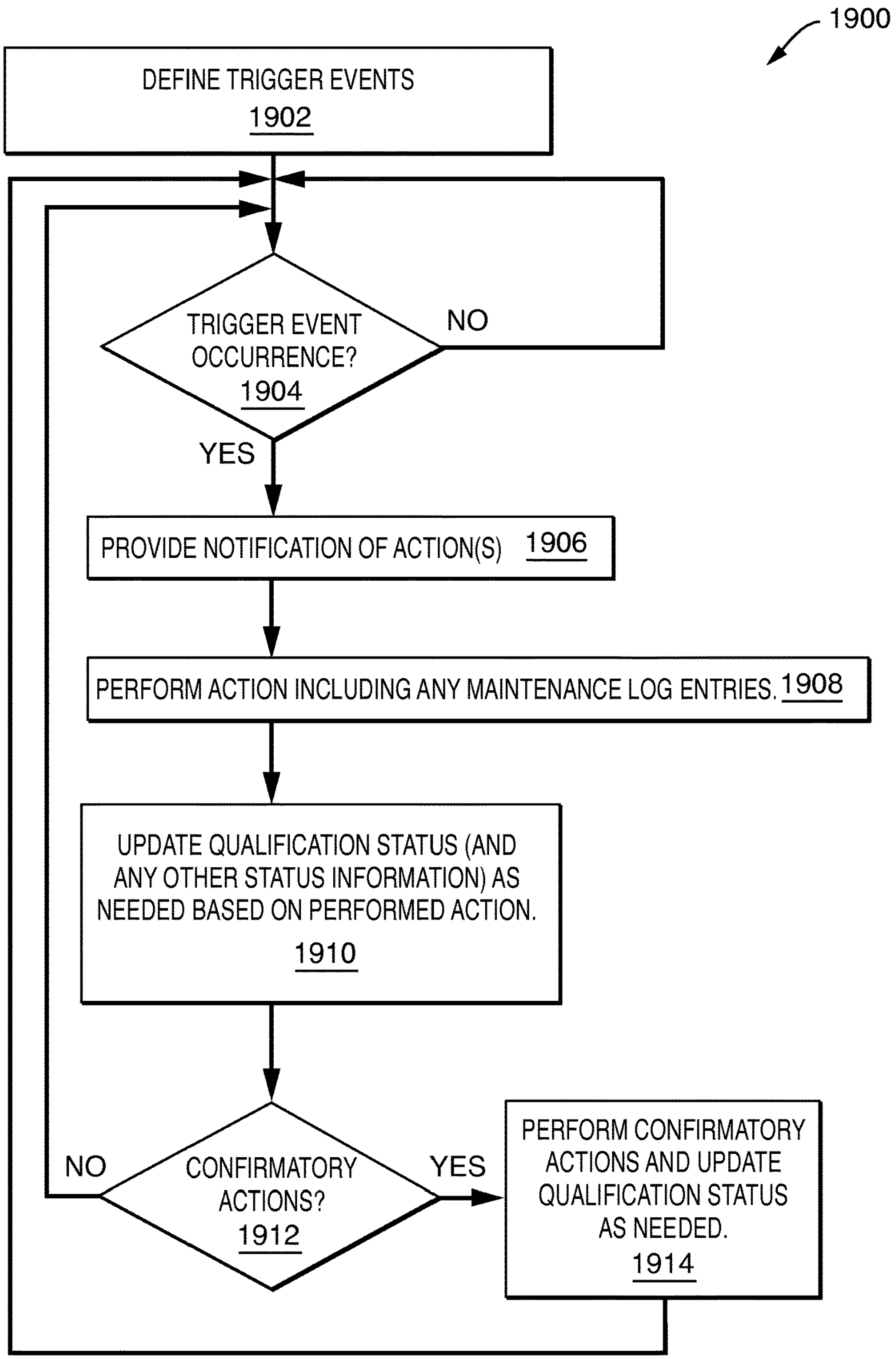
FIG. 20 is a flowchart of processing steps that may be performed in an embodiment in accordance with techniques herein.

Referring to FIG. 20, shown is a flowchart of processing steps that may be performed in an embodiment in accordance with techniques herein. The flowchart 1900 summarizes one sequence of processing steps that may be performed in an embodiment as described above. At step 1902, one or more trigger events may be defined. As described above, such trigger events may be performance-based, time-based, usage-based, and the like. The trigger events may be defined as defaults in a system and/or include ones defined by a customer or user. At step 1904, a determination is made as to whether a trigger event has occurred. If not, processing waits at step 1904 until such event has occurred. Once a trigger event has occurred, control proceeds to step 1906 to provide notification to a user, such as through a user interface (UI) indicator and/or other means, that such action(s) is/are to be performed. As an example noted above, a device may be used a specified number of times triggering an occurrence of a usage-based event. Notification may be provided to the user such as through a UI indicator indicating that a maintenance activity is due (e.g., date of next maintenance indicates current date/time, setting a device or component qualification status UI indicator to unqualified or unknown). At step 1908, a user performs the one or more actions including creating any maintenance log entries as may be appropriate for the action(s) performed. For example, the action performed in step 1908 may include performing a maintenance activity and logging such activity. The action performed in steps 1908 may alternatively be to simply perform one or more requalification or other tests without requiring maintenance and/or repair for a device. At step 1910, the qualification status for the affected device is updated as needed based on the performed action in step 1908. For example, if the action is a maintenance activity having a particular severity level, defined qualification/requalification criteria may indicate to update the device qualification status to unqualified until subsequent confirmatory actions are performed. As another example, the action may be to perform one or more qualification tests with respect to a device without any maintenance activities and one or more such tests may fail/have erroneous results. As such, step 1910 may include updating the device's qualification status to unqualified until at a later point in time at which such qualification tests are successfully completed. At step 1912, it is determined whether confirmatory actions are to be performed in response to performing the initial set of one or more actions in steps 1908 and updating the qualification status in step 1910 (e.g., such as setting the qualification status of a device to unqualified, unknown, or another state other than qualified). If step 1914 evaluates to yes, control proceeds to step 1914 to perform the confirmatory action(s) and accordingly update the qualification status. From step 1914, control proceeds to step 1904 to wait for the next trigger event occurrence. If step 1912 evaluates to no, control proceeds to step 1904.

It should be noted that variations to the general processing described in FIG. 20 are described above. For example, step 1910 may also include updating one or more other items of device or component status information. To further illustrate as described above, policy information in a system may be defined to set one or more other status indicators reflecting a device as offline or otherwise unavailable for current use if the device is unqualified or, more generally, in any other qualification state besides "qualified" (as may be the case in an embodiment having more qualification states than qualified and unqualified as well as states relating to verification, validation, and calibration).

Depending on the particular confirmatory actions, if any, the qualification status described above may more generally indicate a compliance status based not only on qualification testing requirements and results, but also other aspects of compliance such as may be related to, for example, verification, validation, and/or calibration of a device, system, or component or module of a system. For example, an embodiment may have a single compliance status having a value of compliant or not compliant. In order for a device, such as an MS or LC system, to be compliant, the device must also be in compliance with all verification, validation and calibration testing that may be required. Otherwise, the device may have a compliance status of not compliant. As another example, an embodiment may have a single overall compliance status that is any of compliant, not compliant and partially compliant. In order to be compliant, the device must be in compliance with all verification, validation and calibration testing as described above. Alternatively, a device may have a state of partially compliant if the device is in compliance with at least one requirement related to qualification, verification, calibration or validation (e.g., pass at least one qualification test related to IQ, OQ or PQ). If the device is not in compliance with at least one requirement related to qualification, verification, calibration or validation, the device has a compliance status of not compliant. If the device has a status of not compliant or partially compliant, an embodiment may provide further more detailed compliance status information regarding the different compliance aspects affecting or used in determining the overall compliance status. For example, the embodiment may provide a separate status indication regarding each of qualification, verification, calibration, and validation as may be suitable for a particular device. In this manner, for example, if a device has an overall compliance status of partially compliant, one may use the separate status indicators to evaluate what aspects of the device currently meet or pass requirements for each of the different aspects used in determining the overall compliance status.

In connection with the above-noted compliance status, the occurrence of a trigger event and/or performing an action may have any one of a variety of different affects upon the overall compliance status and/or any separate status indicators. For example, upon the occurrence of a trigger event, a device may transition to an overall compliance state of not compliant until a particular action and any associated confirmatory actions have been successfully completed. As another example, upon the occurrence of a trigger event, the device may maintain its current overall compliance status and a user may be notified to perform an action responsive to the trigger event. Once the action has been performed, the overall compliance status as well as any appropriate individual status indicators may be updated. For example, if the action is a maintenance activity, the device overall compliance status as well as the individual qualification status indicator may transition to not compliant until requalification is successfully performed.

Figure 21:
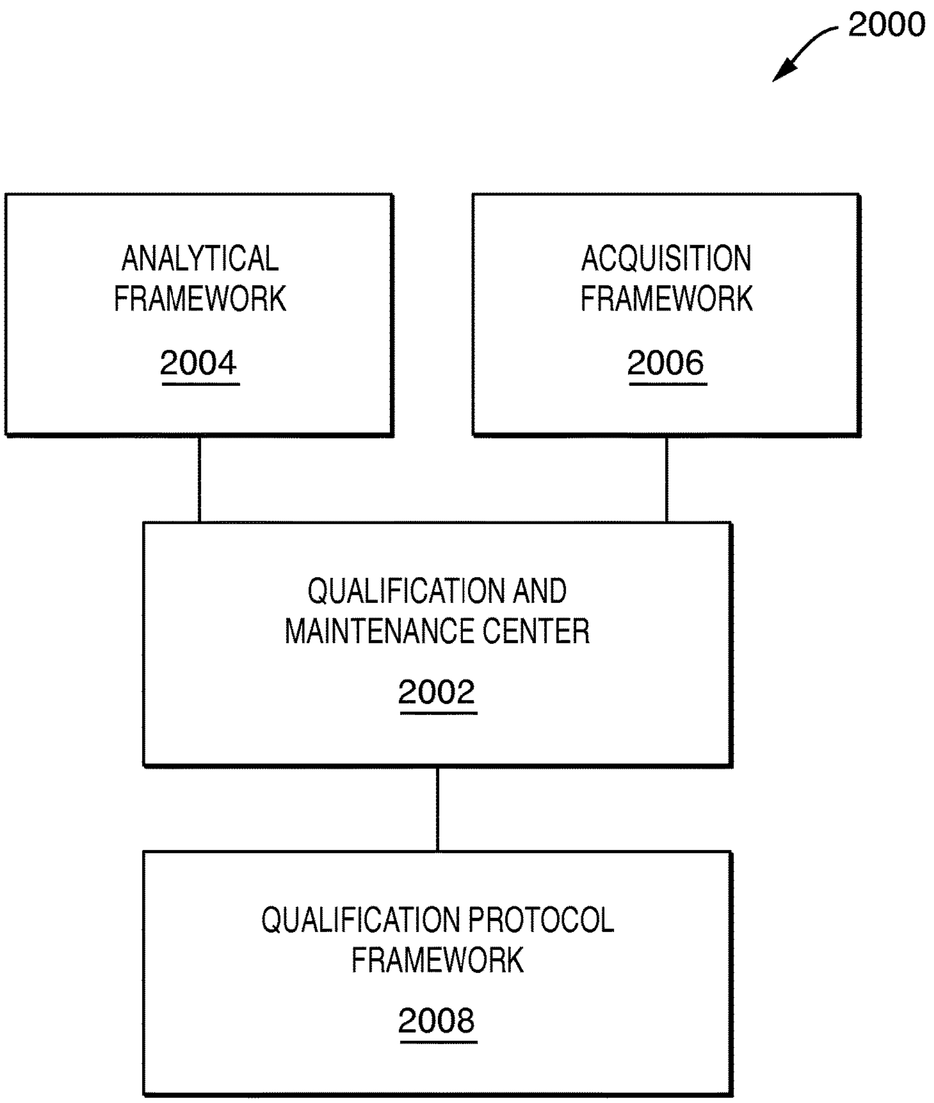
FIG. 21 is an example of components that may be included in an embodiment in accordance with techniques herein.

Referring to FIG. 21, shown is an example of software components that may be included an embodiment in accordance with techniques herein. The example 2000 illustrates one architecture of components that may be used in an embodiment in accordance with techniques herein and includes an analytical framework 2004, acquisition framework 2006, qualification and maintenance center 2002, and qualification protocol framework 2008. The user interface and screenshots described and illustrated herein may be included in the qualification and maintenance center 2002. The component 2002 communicates with components 2004, 2006 and/or 2008 as needed during operation. For example, component 2002 communicates with the qualification protocol framework 2008 as part of qualification test processing such as using a qualification protocol to obtain the qualification tests and instructions. Component 2002 may communicate with the analytical framework 2004 when executing the qualification tests for devices other than instruments. Component 2002 may communicate with the acquisition framework 2006 when executing the qualification tests for instruments described herein. Although not illustrated, data may be stored and/or retrieved from data containers such as databases by any of the components. For example, component 2008 may store and retrieve information about qualification protocols from a database.

It should also be noted that embodiments are described herein with data systems and scientific instruments such as may be used in connection with sample analysis. More generally, the techniques herein may be used in embodiments with any type of instrument or other device, as well as in connection with other software systems.

The techniques herein may be performed by executing code which is stored on any one or more different forms of computer-readable media. Computer-readable media may include different forms of volatile (e.g., RAM) and non-volatile (e.g., ROM, flash memory, magnetic or optical disks, or tape) storage which may be removable or non-removable.

While the invention has been disclosed in connection with preferred embodiments shown and described in detail, their modifications and improvements thereon will become readily apparent to those skilled in the art. Accordingly, the spirit and scope of the present invention should be limited only by the following claims.

What is claimed is:

1. A computer-implemented method for determining a qualification status of a device, comprising, by at least one processor:

receiving a policy comprising a plurality of severity levels, each of the plurality of severity levels indicating whether requalification of the device is required responsive to performance of at least one activity on the device, the at least one activity linked to a qualification procedure used for performing one or more qualification tests for the device and comprising at least one repair activity or at least one maintenance activity;

determining an occurrence of a trigger event requiring performance of the at least one activity for the device;

receiving an indication of completion of the performance of the at least one activity on the device;

determining a severity level associated with the at least one activity;

setting the qualification status of the device to unqualified responsive to the severity level indicating that requalification of the device is required; and updating the qualification status of the device based on results of the one or more qualification tests.

2. The method of claim 1, further comprising:

disabling the device from further use responsive to the qualification status of the device being set to unqualified; and enabling the device responsive to one or more subsequent confirmatory actions being successfully performed.

3. The method of claim 1, wherein the qualification status of the device comprises qualification of regulatory requirements of a regulatory entity.

4. The method of claim 3, the regulatory requirements comprising Food and Drug Administration (FDA) requirements.

5. The method of claim 4, the regulatory requirements comprising at least one of 21 Code of Federal Regulations (CFR) Part 211, 21 CFR Part 11, or 21 CFR Part 820.

6. The method of claim 1, wherein said device is a scientific laboratory instrument.

7. The method of claim 6, wherein said device is a scientific laboratory instrument that performs any of liquid chromatography, gas chromatography, mass spectrometry, supercritical fluid chromatography, capillary electrophoresis, and analog to digital signal conversion and/or transmission.

8. The method of claim 1, wherein said device is a computer system.

9. The method of claim 1, wherein the trigger event comprises a time-based event based on a planned or scheduled event.

10. The method of claim 1, wherein the trigger event comprises a usage-based event based on a planned or scheduled event that depends on an amount of usage of at least a portion of the device.

11. The method of claim 1, wherein an occurrence of a performance-based event depends on whether the device meets specified performance criteria.

12. The method of claim 1, wherein the trigger event comprises an unscheduled event for the device is an unscheduled repair, unscheduled update, or unscheduled upgrade.

13. The method of claim 1, wherein the trigger event is based on an observed trend over a time period associated with an amount of downtime of the device.

14. The method of claim 1, wherein the trigger event is based on an observed trend over a time period associated with analytical results generated by the device.

15. The method of claim 1, the device comprising at least one of a liquid chromatography (LC) device or a mass spectrometry (MS) device.

16. The method of claim 15, the trigger event generated based on performance criteria of the device.

17. The method of claim 16, the performance criteria comprising mass accuracy performance associated with the device.

18. The method of claim 16, the performance criteria comprising peak tailing associated with the device.

19. The method of claim 15, the trigger event generated based on analysis of a control sample by the device.

20. The method of claim 1, the trigger event generated based on a user-defined number of uses of a component of the device.

21. An apparatus comprising:

one or more computer systems operatively coupled to at least one device; and a computer readable medium comprising code stored thereon that, when executed by at least one processor, causes the one or more computer systems to:

receive a policy comprising a plurality of severity levels, each of the plurality of severity levels indicating whether requalification of the device is required responsive to performance of at least one activity on the device, the at least one activity linked to a qualification procedure used for performing one or more qualification tests for the device and comprising at least one repair activity or at least one maintenance activity;

determine an occurrence of a trigger event requiring performance of the at least one activity for the device;

receive an indication of completion of the performance of the at least one activity on the device;

determine a severity level associated with the at least one activity;

set the qualification status of the device to unqualified responsive to the severity level indicating that requalification of the device is required; and update the qualification status of the device based on results of the one or more qualification tests.

22. The apparatus of claim 21, the device comprising at least one of a liquid chromatography (LC) device or a mass spectrometry (MS) device.

23. The apparatus of claim 21, the trigger event generated based on performance criteria of the device, the performance criteria comprising mass accuracy performance associated with the device.

24. The apparatus of claim 23, the trigger event generated based on performance criteria of the device, the performance criteria comprising peak tailing associated with the device.

25. The apparatus of claim 23, the trigger event associated with analysis of a control sample by the device.

26. The apparatus of claim 21, the trigger event associated with a user-defined number of uses of a component of the device.

27. A non-transitory computer readable medium comprising code stored thereon that, when executed by at least one processor of a computing device, causes the computing device to perform a method for determining a qualification status of a device, the method comprising:

receiving a policy comprising a plurality of severity levels, each of the plurality of severity levels indicating whether requalification of the device is required responsive to performance of at least one activity on the device, the at least one activity linked to a qualification procedure used for performing one or more qualification tests for the device and comprising at least one repair activity or at least one maintenance activity;

determining an occurrence of a trigger event requiring performance of the at least one activity for the device;

receiving an indication of completion of the performance of the at least one activity on the device;

determining a severity level associated with the at least one activity;

setting the qualification status of the device to unqualified responsive to the severity level indicating that requalification of the device is required; and updating the qualification status of the device based on results of the one or more qualification tests.

* * * * *